(12) United States Patent
Tsunoda et al.

(10) Patent No.: US 11,529,266 B2
(45) Date of Patent: Dec. 20, 2022

(54) ELASTIC MEMBER AND DISPOSABLE WEARING ARTICLE INCLUDING ELASTIC MEMBER

(71) Applicant: Daio Paper Corporation, Ehime (JP)

(72) Inventors: Arika Tsunoda, Tochigi (JP);
Syunsuke Sakai, Tochigi (JP)

(73) Assignee: Daio Paper Corporation, Ehime (JP)

( * ) Notice: Subject to any disclaimer, the term of this patent is extended or adjusted under 35 U.S.C. 154(b) by 364 days.

(21) Appl. No.: 16/637,529

(22) PCT Filed: Sep. 25, 2018

(86) PCT No.: PCT/JP2018/035312
§ 371 (c)(1),
(2) Date: Feb. 7, 2020

(87) PCT Pub. No.: WO2019/065575
PCT Pub. Date: Apr. 4, 2019

(65) Prior Publication Data
US 2020/0214904 A1 Jul. 9, 2020

(30) Foreign Application Priority Data

Sep. 27, 2017 (JP) .............................. JP2017-187179
Mar. 19, 2018 (JP) .............................. JP2018-051155

(51) Int. Cl.
*B32B 3/24* (2006.01)
*B32B 5/02* (2006.01)
(Continued)

(52) U.S. Cl.
CPC ............ *A61F 13/496* (2013.01); *A61F 13/49* (2013.01); *A61F 13/4902* (2013.01);
(Continued)

(58) Field of Classification Search
None
See application file for complete search history.

(56) References Cited

U.S. PATENT DOCUMENTS 4,743,241 A * 5/1988 Igaue .................. A61F 13/4963
604/385.26
5,807,368 A * 9/1998 Helmer ................. A61F 13/496
604/385.24
(Continued)

FOREIGN PATENT DOCUMENTS

CN 102371741 A * 3/2012 ......... A61F 13/4902
DE 432986 C * 8/1926 ......... A61F 13/4902
(Continued)

OTHER PUBLICATIONS

International Search Report for PCT/JP2018/035312, dated Nov. 13, 2018.

*Primary Examiner* — Jeffrey A Vonch
(74) *Attorney, Agent, or Firm* — Andrus Intellectual Property Law, LLP

(57) ABSTRACT

An elastic sheet stretchable structure in which a first sheet layer and a second sheet layer are bonded through joint holes penetrating an elastic film at a plurality of sheet joined portions arranged at intervals is included. Joined portion groups in the stretchable region are in a relationship of intersecting a stretchable direction line at respective positions in an orthogonal direction or in a relationship of not intersecting the stretchable direction line at a separation width of 0.5 mm or less in the orthogonal direction of the stretchable direction line. The joined portion groups are in a relationship of not intersecting an oblique line at a predetermined separation width in the orthogonal direction in an oblique line group of oblique lines q in the orthogonal (Continued)

direction intersecting the stretchable direction line within an angle range γ of 45 degrees or less.

15 Claims, 25 Drawing Sheets

(51) Int. Cl.

| | |
|---|---|
| B32B 5/24 | (2006.01) |
| B32B 7/05 | (2019.01) |
| B32B 25/10 | (2006.01) |
| B32B 27/12 | (2006.01) |
| A61F 13/49 | (2006.01) |
| A61F 13/496 | (2006.01) |
| B32B 7/022 | (2019.01) |
| B32B 7/03 | (2019.01) |
| B32B 3/26 | (2006.01) |
| B32B 37/00 | (2006.01) |
| A41B 9/00 | (2006.01) |
| B29C 65/08 | (2006.01) |
| B29C 65/00 | (2006.01) |
| B29L 31/48 | (2006.01) |
| A61F 13/51 | (2006.01) |
| B32B 5/14 | (2006.01) |
| A61F 13/15 | (2006.01) |

(52) U.S. Cl.
CPC .. *A61F 13/49009* (2013.01); *A61F 13/49011* (2013.01); *A61F 13/49015* (2013.01); *A61F 13/49019* (2013.01); *B32B 3/266* (2013.01); *B32B 5/022* (2013.01); *B32B 5/24* (2013.01); *B32B 7/022* (2019.01); *B32B 7/03* (2019.01); *B32B 7/05* (2019.01); *B32B 25/10* (2013.01); *B32B 27/12* (2013.01); *B32B 37/0076* (2013.01); *A41B 9/001* (2013.01); *A41B 2300/22* (2013.01); *A61F 13/51* (2013.01); *A61F 2013/15195* (2013.01); *A61F 2013/49022* (2013.01); *A61F 2013/49033* (2013.01); *A61F 2013/49036* (2013.01); *B29C 65/086* (2013.01); *B29C 66/1122* (2013.01); *B29C 66/21* (2013.01); *B29C 66/344* (2013.01); *B29C 66/41* (2013.01); *B29C 66/7294* (2013.01); *B29C 66/81429* (2013.01); *B29C 66/81433* (2013.01); *B29C 66/83511* (2013.01); *B29L 2031/4878* (2013.01); *B32B 5/145* (2013.01); *B32B 2250/03* (2013.01); *B32B 2250/40* (2013.01); *B32B 2250/44* (2013.01); *B32B 2274/00* (2013.01); *B32B 2307/51* (2013.01); *B32B 2555/02* (2013.01); *Y10T 428/24331* (2015.01); *Y10T 428/24347* (2015.01); *Y10T 428/24826* (2015.01); *Y10T 428/24942* (2015.01); *Y10T 442/659* (2015.04); *Y10T 442/671* (2015.04); *Y10T 442/674* (2015.04); *Y10T 442/678* (2015.04)

(56) References Cited

U.S. PATENT DOCUMENTS

| | | | | | |
|---|---|---|---|---|---|
| 5,846,232 | A * | 12/1998 | Serbiak | ............. | A61F 13/49009 604/385.29 |
| 5,851,935 | A * | 12/1998 | Srinivasan | ............... | B32B 5/022 442/381 |
| 5,899,896 | A * | 5/1999 | Suprise | ................. | A61F 13/622 604/391 |
| 5,931,827 | A * | 8/1999 | Buell | ................. | A61F 13/49015 604/385.29 |
| 6,069,097 | A * | 5/2000 | Suzuki | .................... | B32B 27/12 442/364 |
| 6,255,236 | B1 * | 7/2001 | Cree | ......................... | B32B 5/26 442/381 |
| 6,610,390 | B1 * | 8/2003 | Kauschke | ................ | D04H 3/14 442/325 |
| 2002/0007164 | A1 * | 1/2002 | Boggs | .................. | A61F 13/496 604/385.27 |
| 2002/0016122 | A1 * | 2/2002 | Curro | ................ | A61F 13/15593 428/103 |
| 2002/0023711 | A1 * | 2/2002 | Tange | ................... | D04H 1/559 156/229 |
| 2002/0086602 | A1 * | 7/2002 | Friderich | ................ | B32B 5/04 442/329 |
| 2003/0004481 | A1 * | 1/2003 | Matsuoka | ......... | A61F 13/51121 442/394 |
| 2003/0136497 | A1 * | 7/2003 | Hamulski | ............. | B32B 37/144 156/309.9 |
| 2004/0044323 | A1 * | 3/2004 | Roessler | ........... | A61F 13/49017 604/385.24 |
| 2005/0215972 | A1 * | 9/2005 | Roe | ..................... | A61F 13/4902 604/385.28 |
| 2006/0057924 | A1 * | 3/2006 | Cheng | ...................... | B32B 5/06 442/361 |
| 2007/0048497 | A1 * | 3/2007 | Zhou | ...................... | B32B 37/12 428/137 |
| 2007/0143972 | A1 * | 6/2007 | Kline | .................... | A61F 13/625 24/442 |
| 2007/0254545 | A1 * | 11/2007 | Martin | ..................... | D04H 1/72 156/290 |
| 2008/0051748 | A1 * | 2/2008 | Black | ..................... | D04H 13/00 156/182 |
| 2008/0095978 | A1 * | 4/2008 | Siqueira | .................. | B32B 27/20 156/181 |
| 2009/0149827 | A1 * | 6/2009 | Mlinar | ................ | A61F 13/4902 604/385.24 |
| 2009/0191779 | A1 * | 7/2009 | Cree | ....................... | B29C 66/21 442/361 |
| 2010/0051170 | A1 * | 3/2010 | Nakakado | ......... | A61F 13/15739 156/73.1 |
| 2010/0163161 | A1 * | 7/2010 | Gilgenbach | ....... | A61F 13/49017 156/155 |
| 2010/0168705 | A1 * | 7/2010 | Stabelfeldt | .......... | A61F 13/4902 604/385.29 |
| 2010/0262102 | A1 * | 10/2010 | Turner | ..................... | B32B 5/04 156/308.2 |
| 2010/0285286 | A1 * | 11/2010 | Middlesworth | ....... | B32B 37/144 428/196 |
| 2011/0160691 | A1 * | 6/2011 | Ng | .......................... | B32B 27/02 264/145 |
| 2012/0168063 | A1 * | 7/2012 | Beuther | ............ | A61F 13/15699 156/163 |
| 2012/0172826 | A1 * | 7/2012 | Ng | .......................... | B32B 5/022 428/156 |
| 2012/0302985 | A1 * | 11/2012 | Mukai | .................... | A61F 13/496 604/385.24 |
| 2013/0079743 | A1 * | 3/2013 | Mukai | .................. | A61F 13/49012 604/385.27 |
| 2013/0138072 | A1 * | 5/2013 | Morimoto | ......... | A61F 13/49011 604/385.29 |
| 2013/0310785 | A1 * | 11/2013 | Wade | ................. | A61F 13/49011 604/385.3 |
| 2014/0093703 | A1 * | 4/2014 | Hanschen | ................ | B32B 25/10 428/221 |
| 2014/0130956 | A1 * | 5/2014 | Floberg | ................. | B29C 65/086 156/164 |
| 2015/0148768 | A1 * | 5/2015 | Fukasawa | ......... | A61F 13/49466 604/385.16 |
| 2015/0164708 | A1 * | 6/2015 | Hashimoto | .......... | A61F 13/4942 604/385.26 |
| 2015/0202095 | A1 * | 7/2015 | Kawakami | ............ | A61F 13/496 604/385.16 |
| 2015/0297422 | A1 * | 10/2015 | Nelson | ................ | A61F 13/4902 604/385.16 |
| 2017/0087029 | A1 * | 3/2017 | Nelson | ................ | B32B 38/1825 |
| 2017/0239105 | A1 * | 8/2017 | Matsumura | ........... | A61F 13/515 |

(56) References Cited

U.S. PATENT DOCUMENTS

| | | | |
|---|---|---|---|
| 2017/0319399 A1* | 11/2017 | Desai | B32B 21/042 |
| 2017/0326832 A1* | 11/2017 | Palzewicz | B32B 27/302 |
| 2017/0348158 A1* | 12/2017 | You | A61F 13/15699 |
| 2017/0362756 A1* | 12/2017 | Moinard | B32B 5/26 |
| 2018/0008481 A1* | 1/2018 | Takahashi | B29C 66/41 |
| 2018/0014979 A1* | 1/2018 | Fujita | B29C 66/81429 |
| 2018/0014984 A1* | 1/2018 | Sakai | B29C 66/21 |
| 2018/0015709 A1* | 1/2018 | Takeuchi | B29C 66/81422 |
| 2018/0028371 A1* | 2/2018 | Takaishi | A61F 13/515 |
| 2018/0078429 A1* | 3/2018 | Matsumura | A61F 13/15 |
| 2018/0168874 A1* | 6/2018 | LaVon | A61F 13/15593 |
| 2018/0243145 A1* | 8/2018 | Wright | A61F 13/49014 |
| 2018/0280209 A1 | 10/2018 | Manabe et al. | |
| 2018/0333313 A1* | 11/2018 | LaVon | A61F 13/565 |
| 2018/0333314 A1* | 11/2018 | LaVon | A61F 13/565 |
| 2019/0117469 A1 | 4/2019 | Kunihiro | |
| 2019/0133846 A1* | 5/2019 | Shirai | A61F 13/4902 |
| 2019/0321240 A1* | 10/2019 | Sakaguchi | A61F 13/15 |
| 2020/0163391 A1* | 5/2020 | Morishita | B32B 38/0012 |

FOREIGN PATENT DOCUMENTS

| | | | | |
|---|---|---|---|---|
| EP | 685586 A2 * | 12/1995 | | A61F 13/4902 |
| JP | 2009-518202 | 5/2009 | | |
| JP | 2015-204982 | 11/2015 | | |
| JP | 5918876 B1 * | 5/2016 | | A61F 13/15 |
| JP | 2016-187385 | 11/2016 | | |
| JP | 5967736 | 11/2016 | | |
| JP | 2017-064130 | 4/2017 | | |
| JP | 2017-064225 | 4/2017 | | |
| JP | 2017-064226 | 4/2017 | | |
| JP | 2017-093732 | 6/2017 | | |
| JP | 2017-196296 | 11/2017 | | |
| WO | WO-2008065953 A2 * | 6/2008 | | A61F 13/15593 |
| WO | WO-2012036599 A1 * | 3/2012 | | A61F 13/4902 |
| WO | WO-2016052416 A1 * | 4/2016 | | A61F 13/49007 |
| WO | 2016-121976 | 8/2016 | | |
| WO | WO-2016121982 A1 * | 8/2016 | | A61F 13/15 |
| WO | WO-2016158751 A1 * | 10/2016 | | A61F 13/49 |

* cited by examiner

[FIG.1]
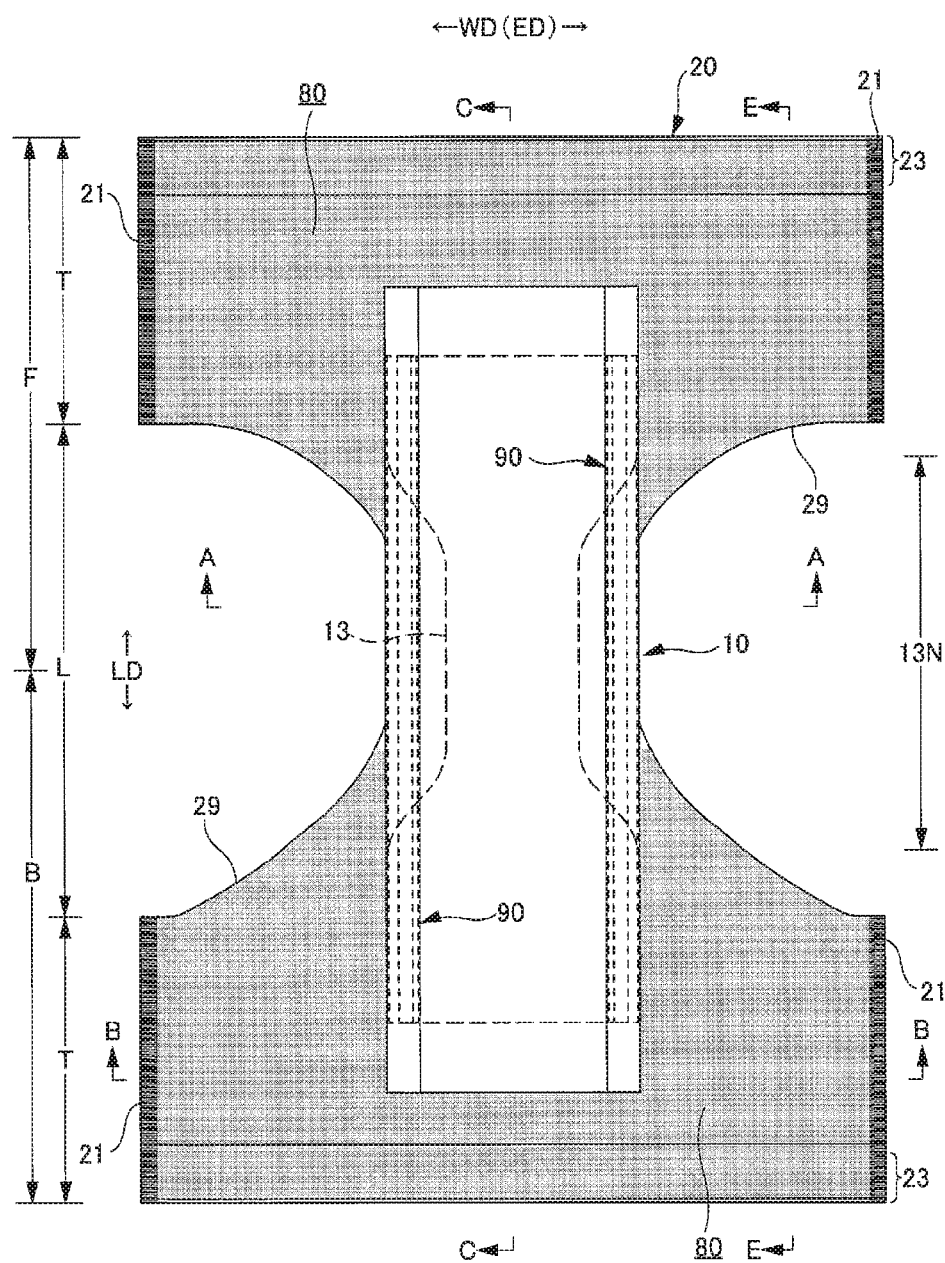

[FIG.2]
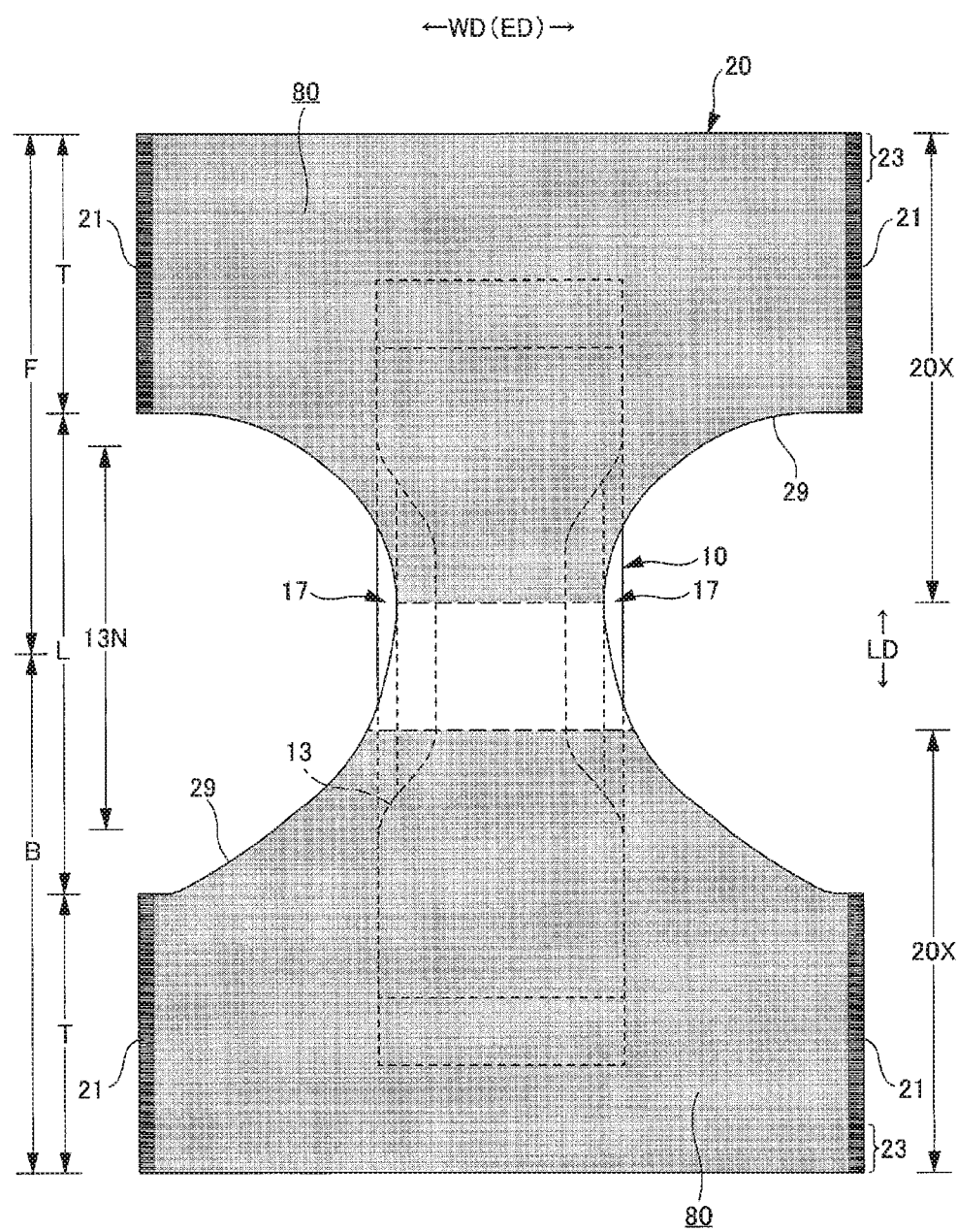

[FIG.3]
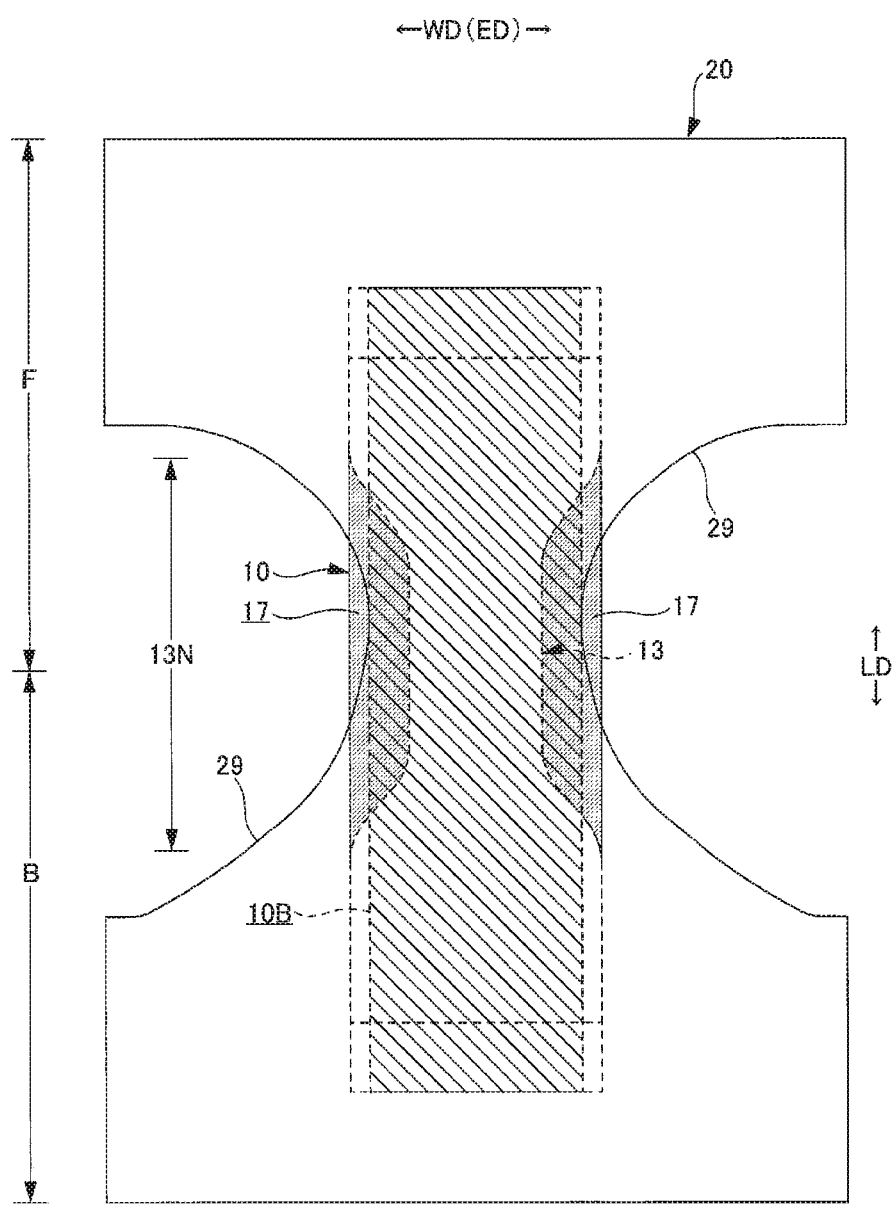

[FIG.4]
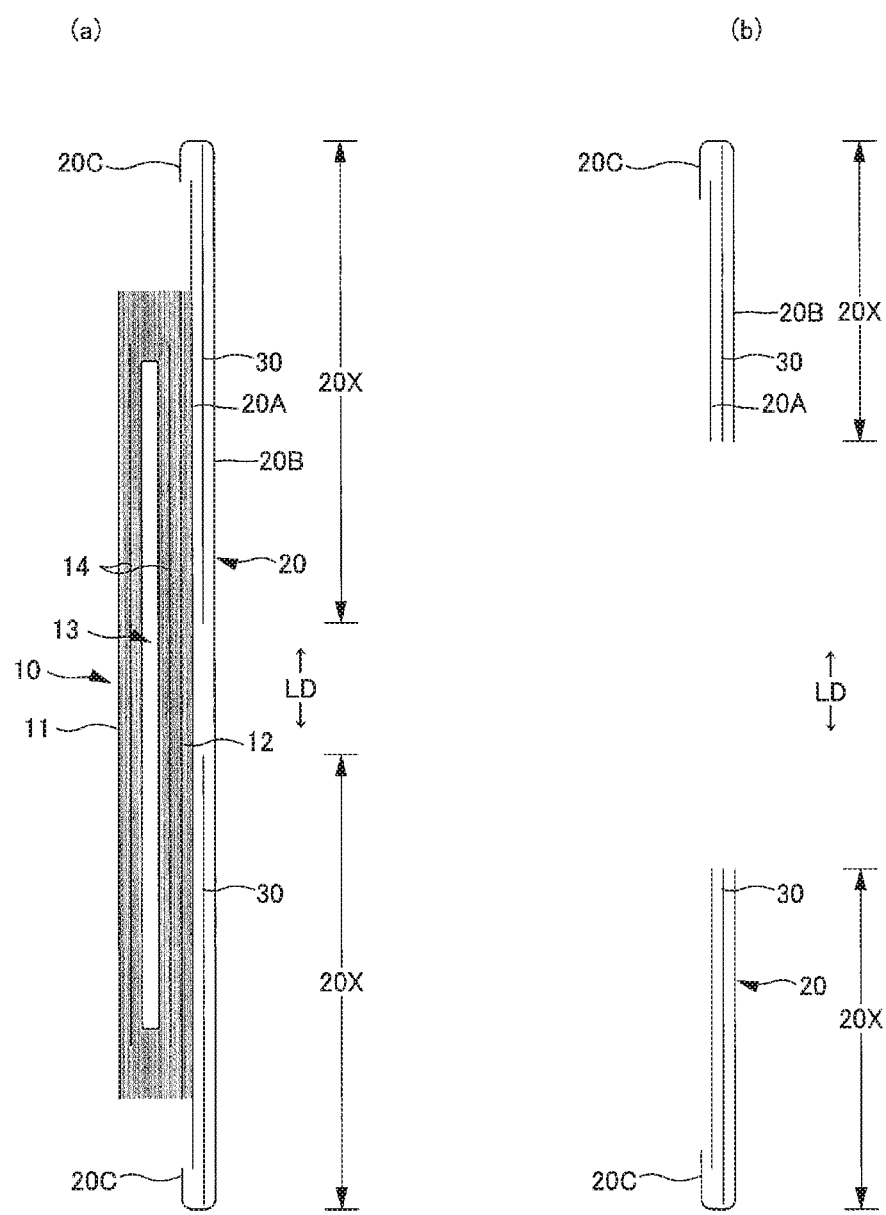

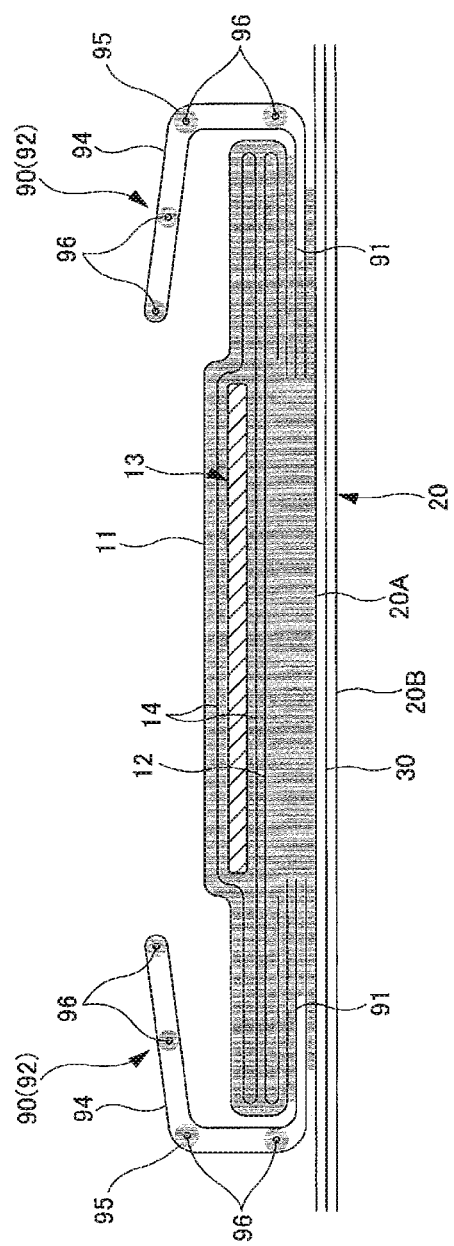

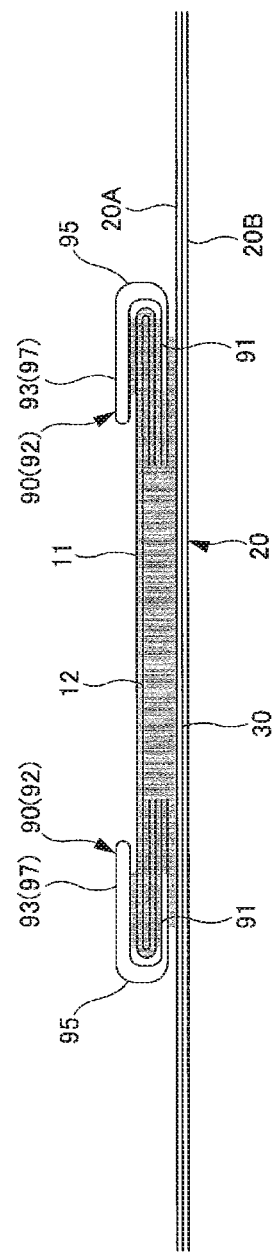

[FIG.7]
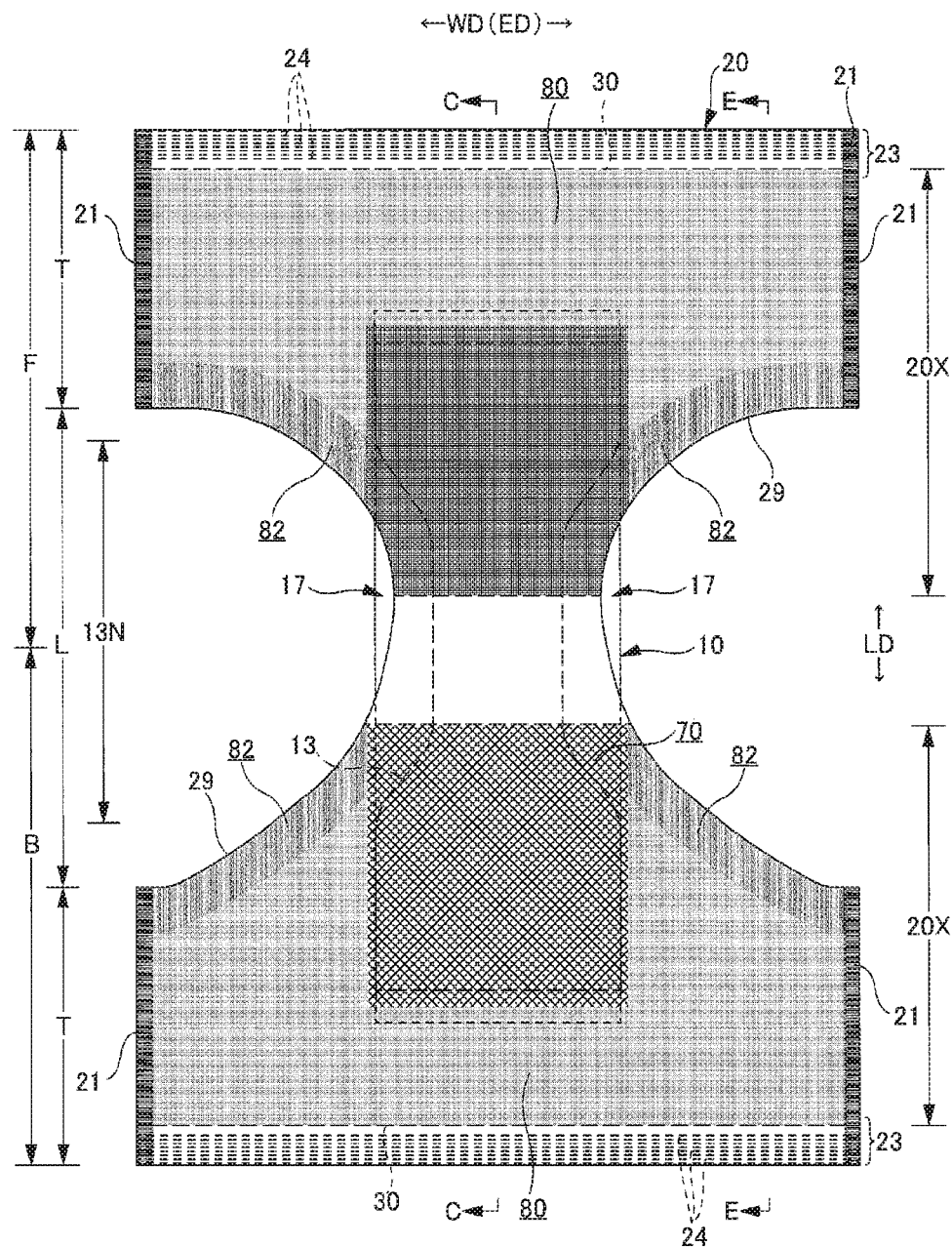

[FIG.8]
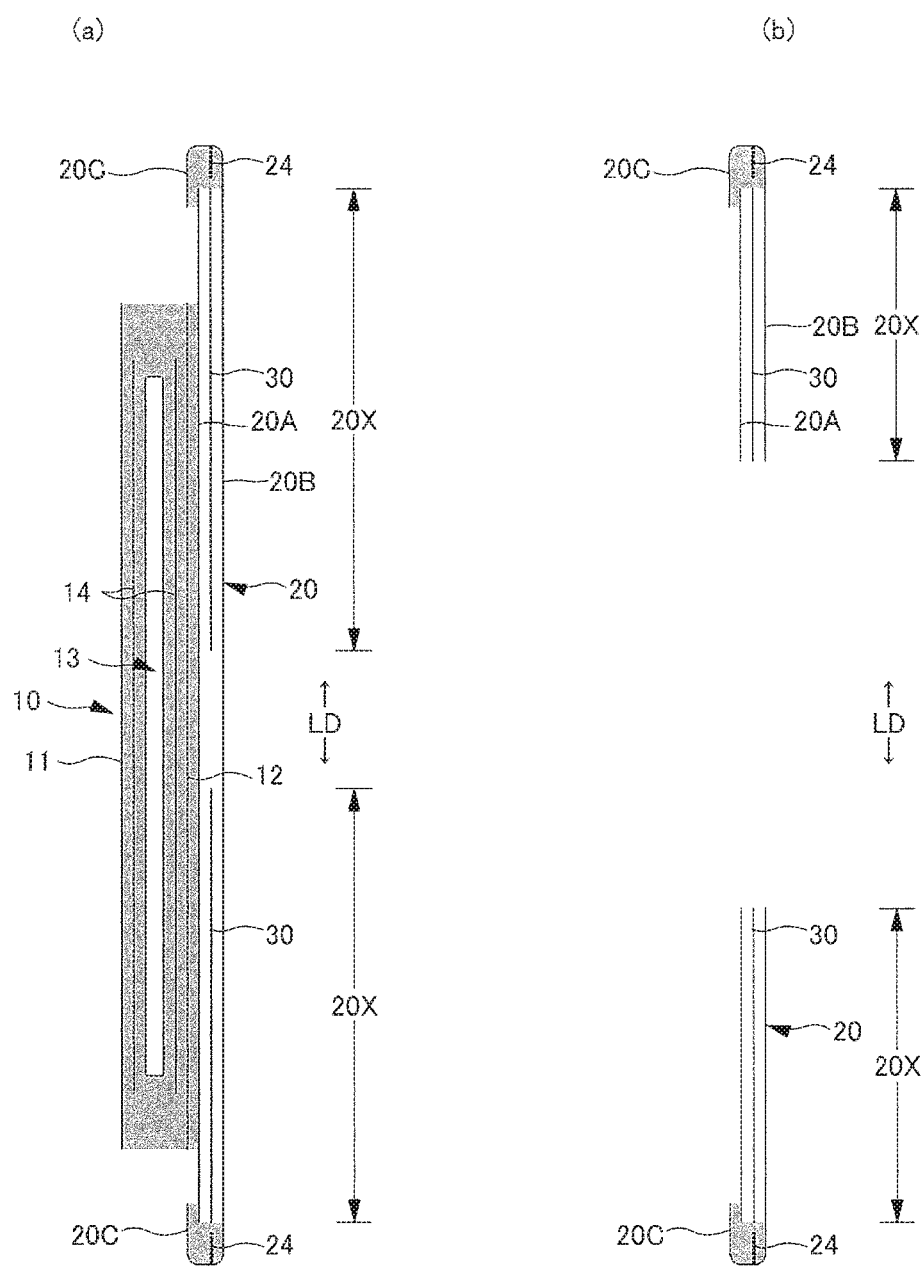

[FIG.9]
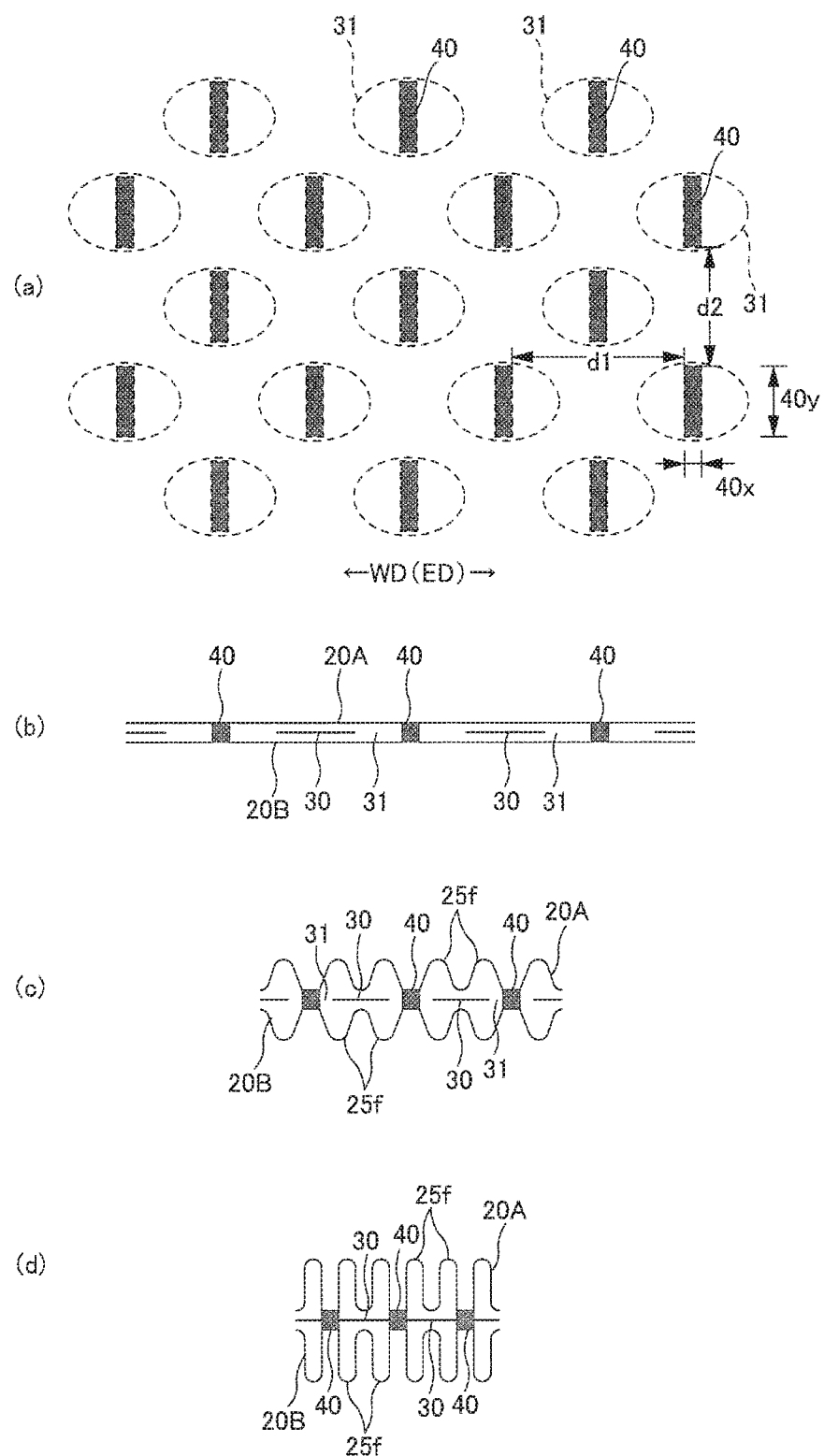

[FIG.10]
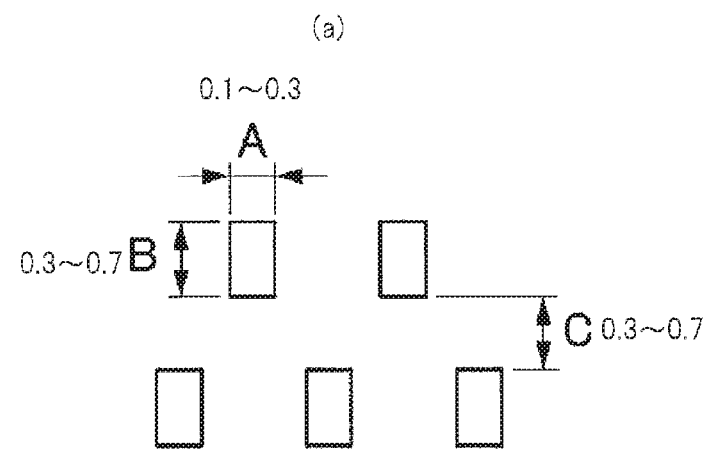
(a)
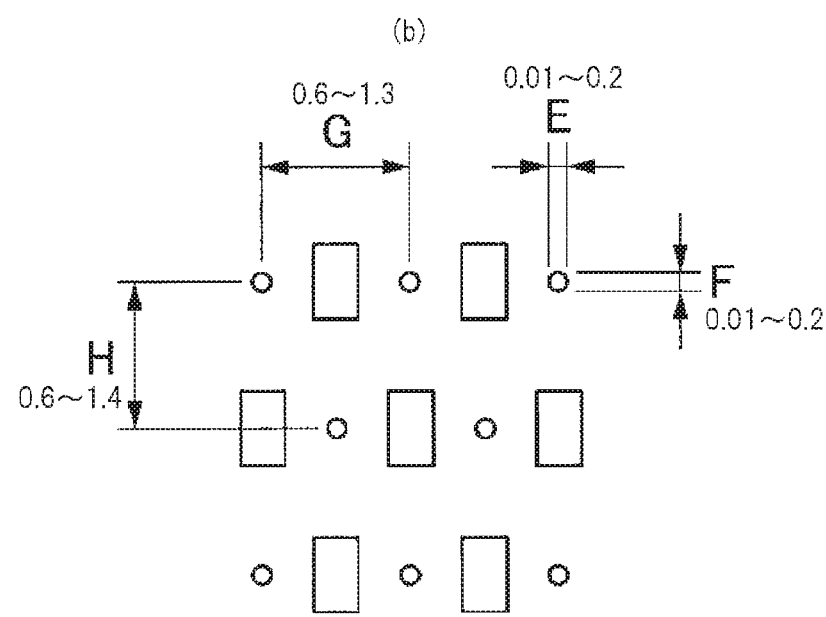
(b)

[FIG.11]
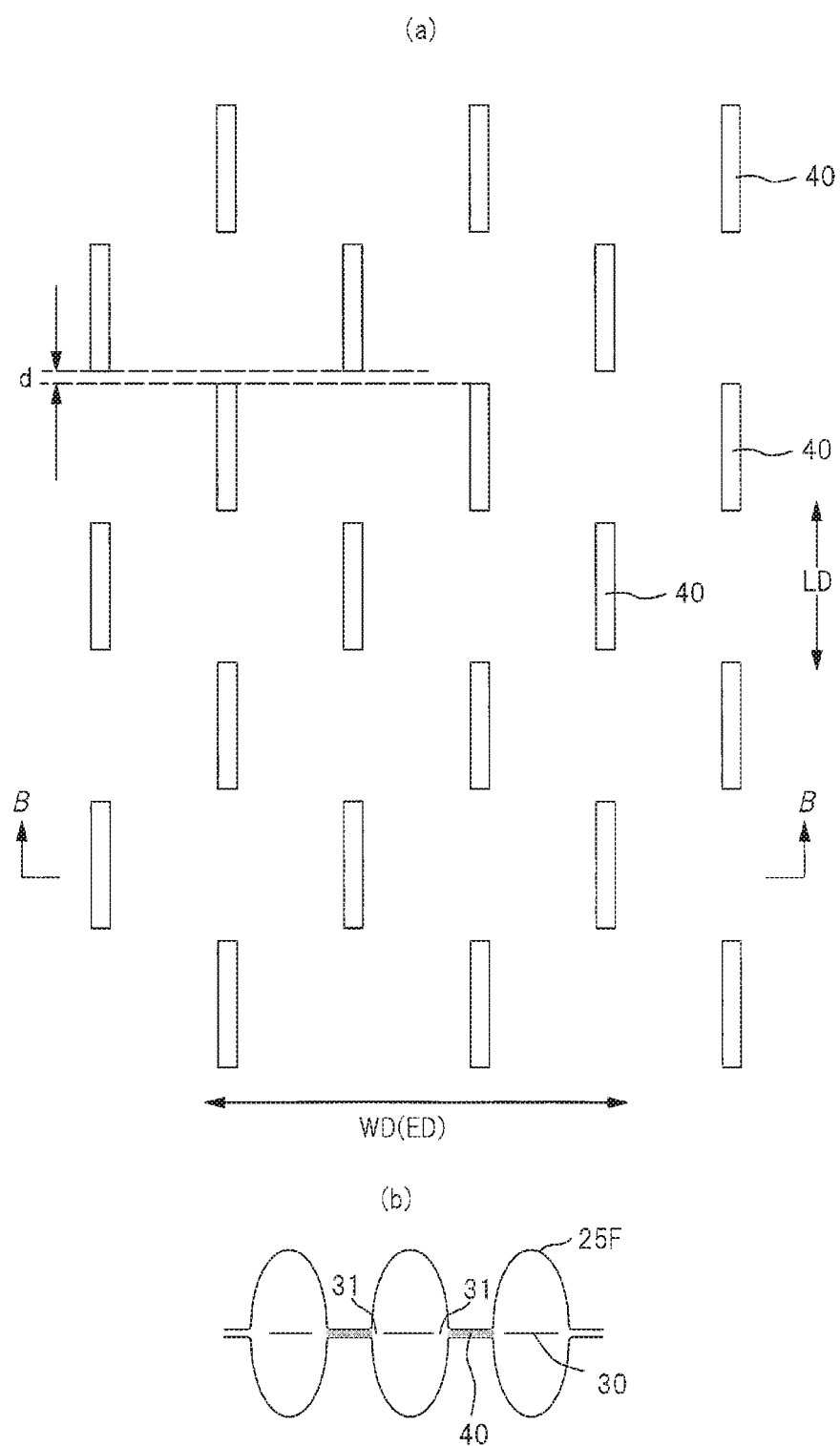

[FIG.12]
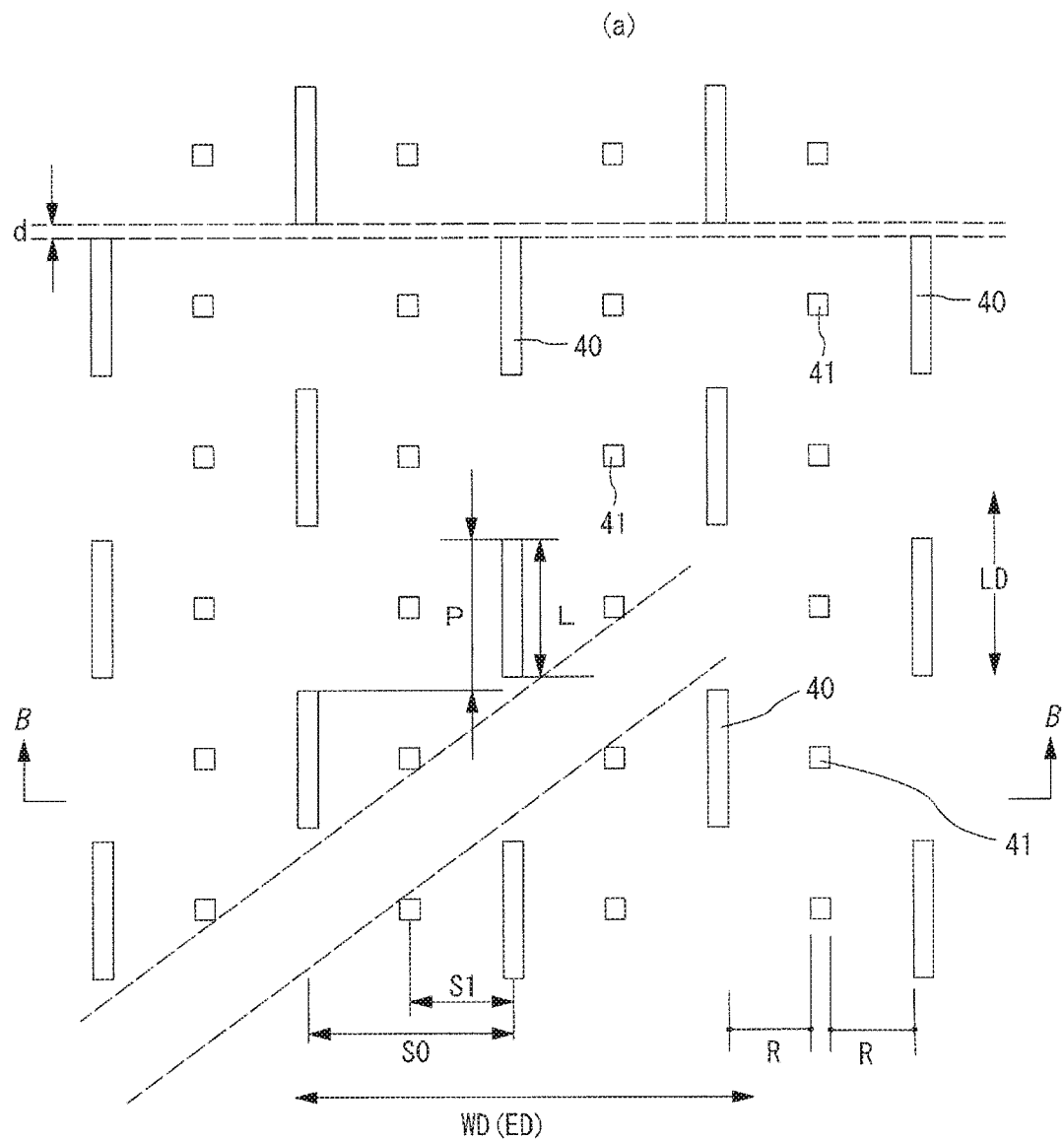
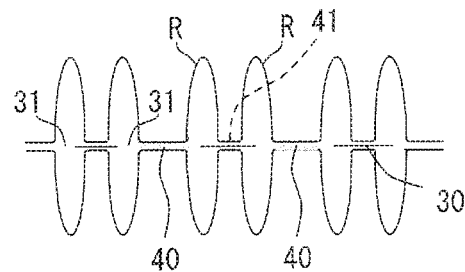

[FIG.13]
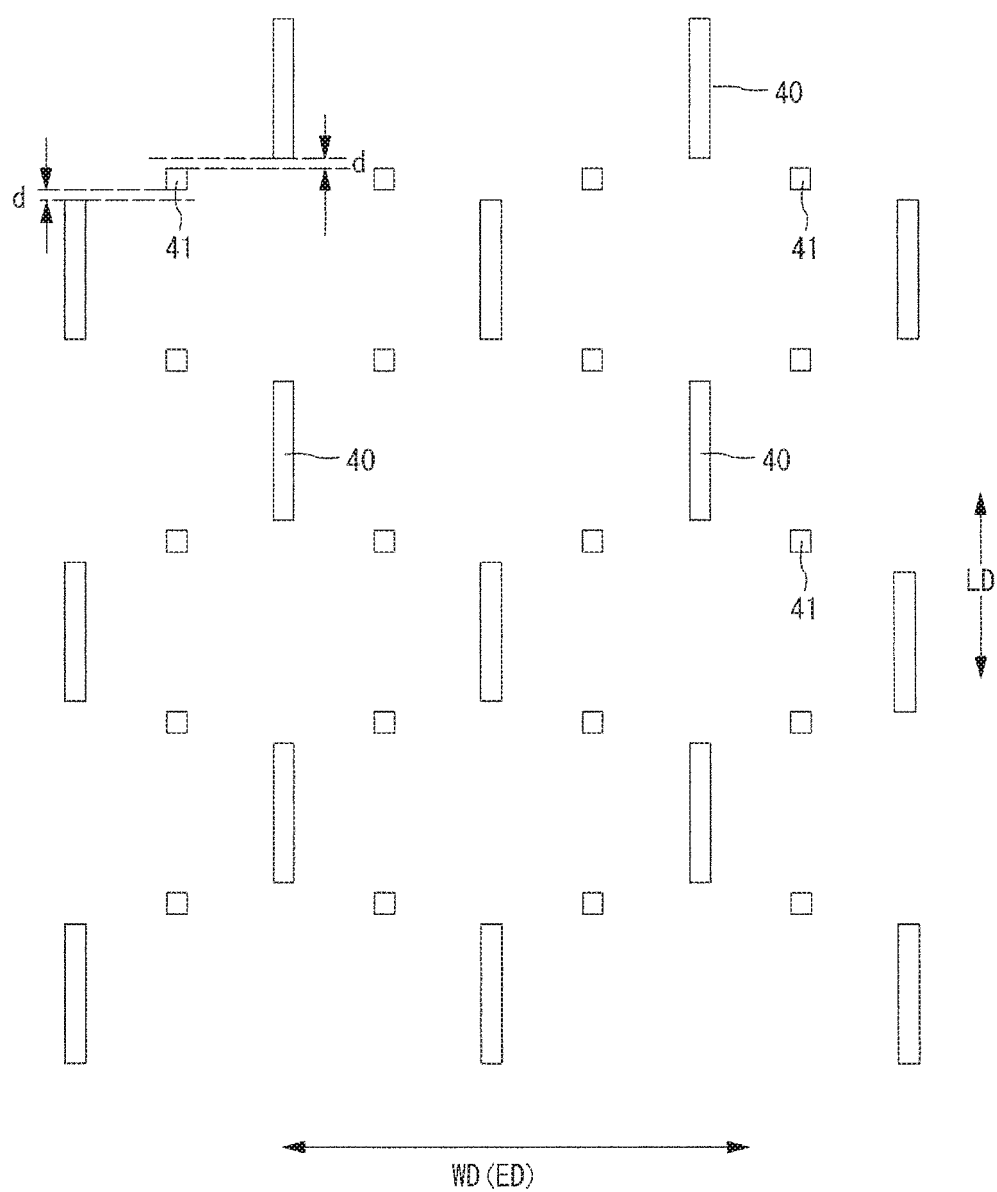

[FIG.14]
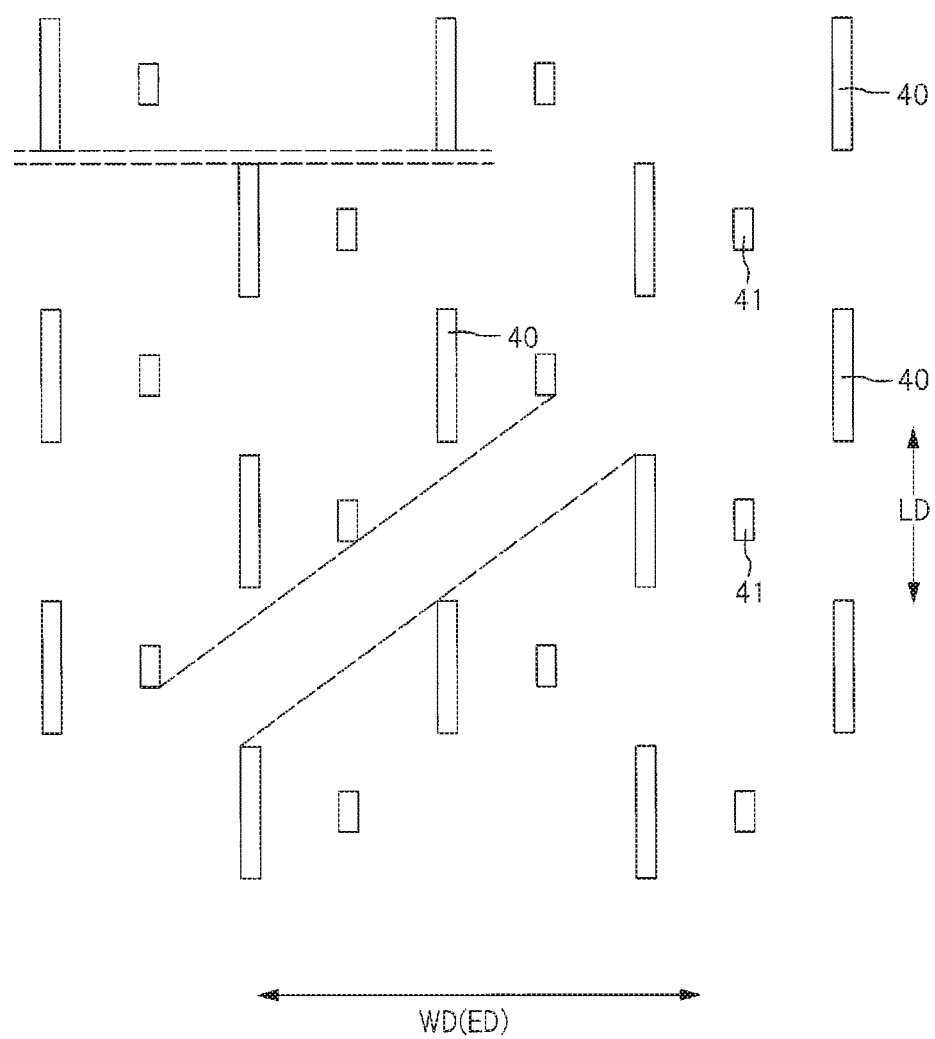

[FIG.15]
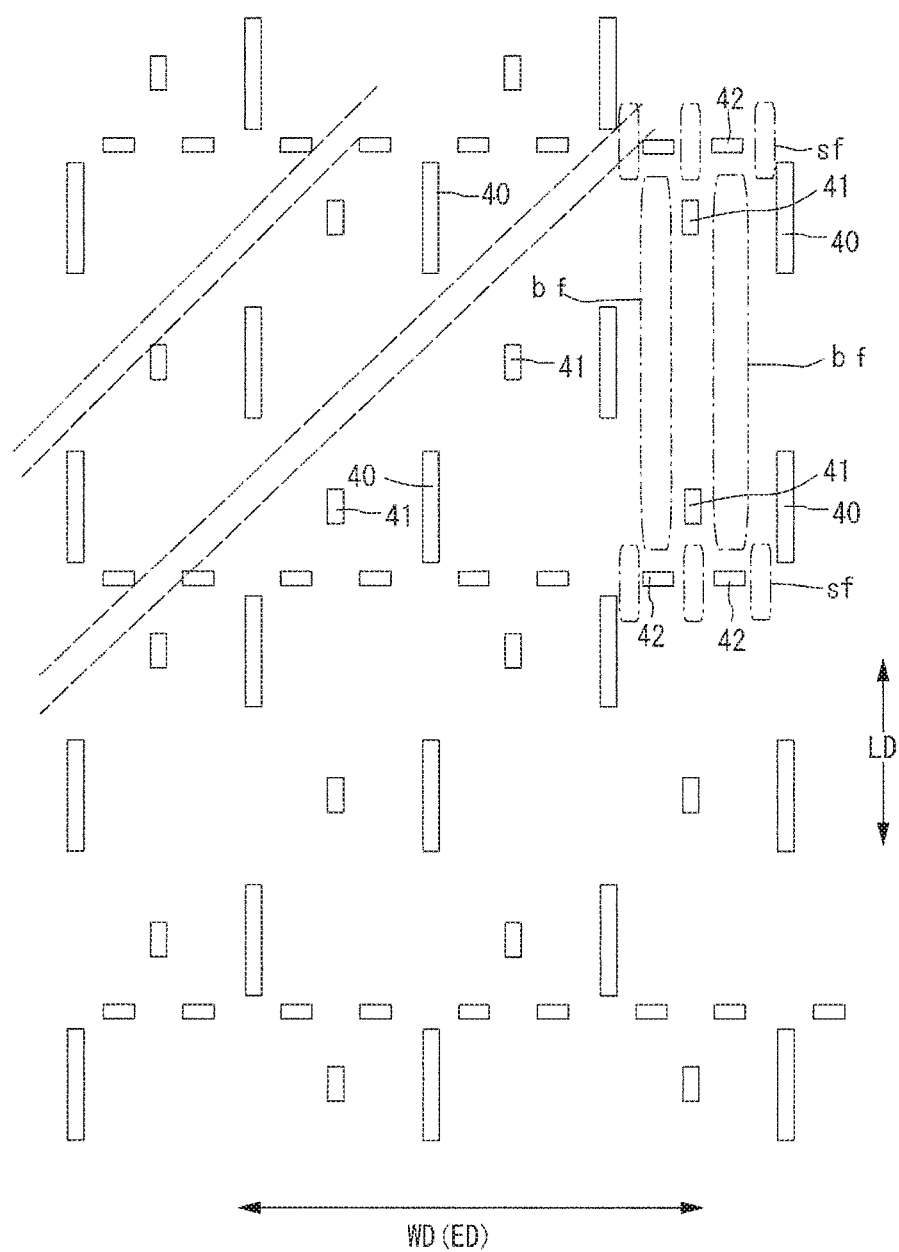

[FIG.16]
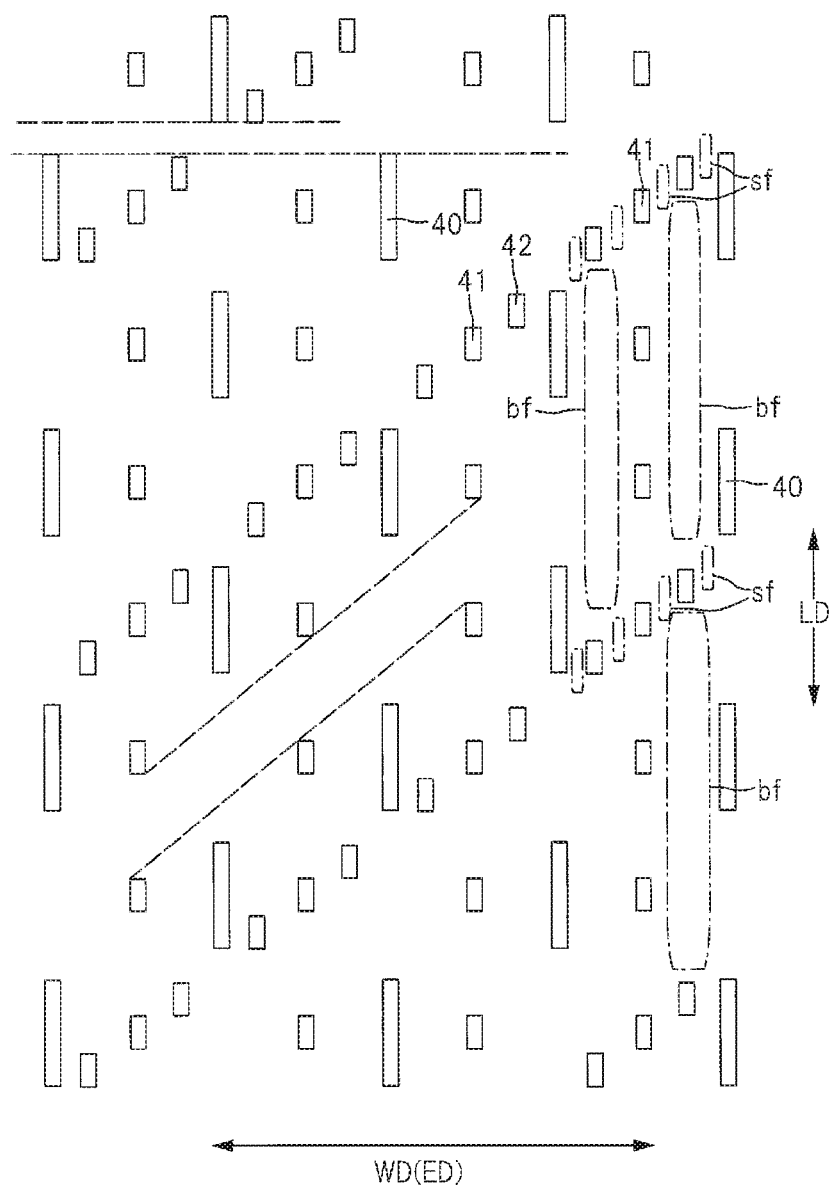

[FIG.17]
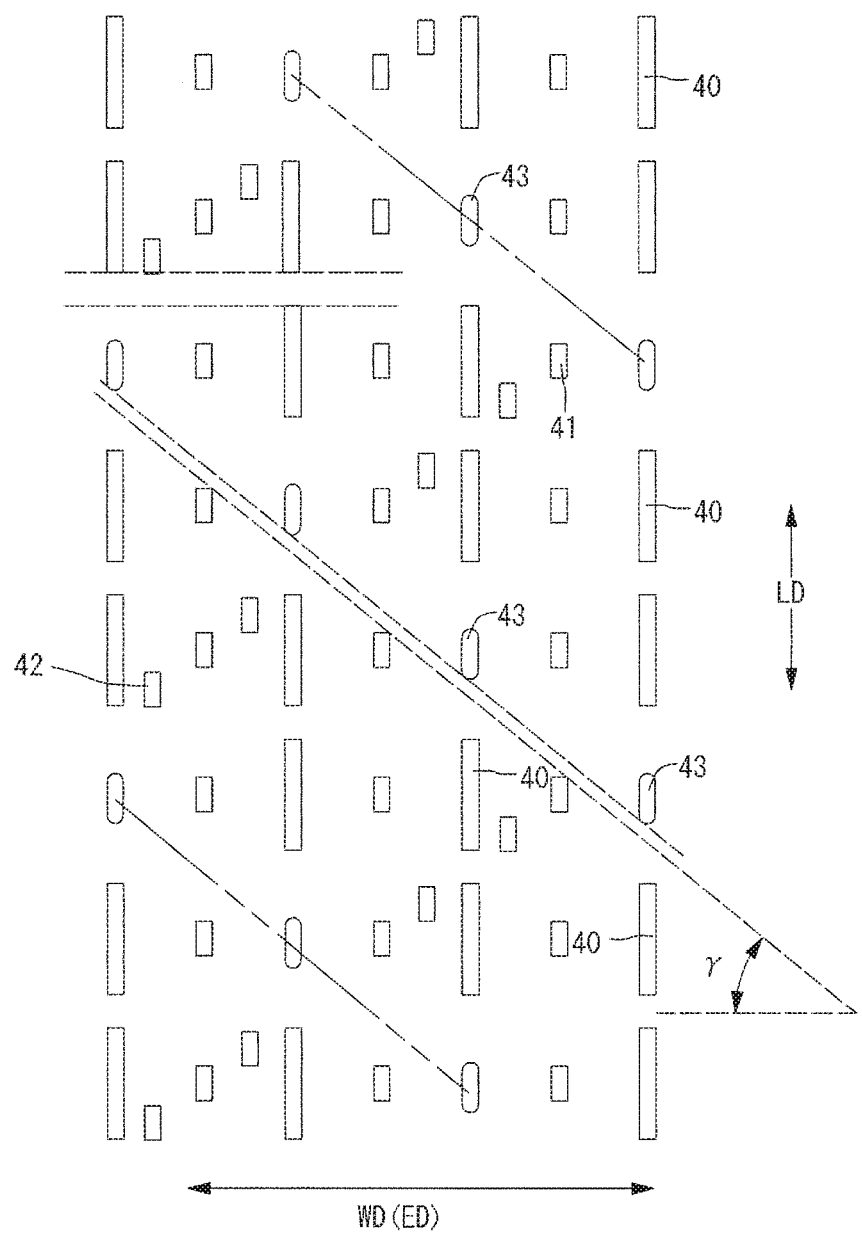

[FIG.18]
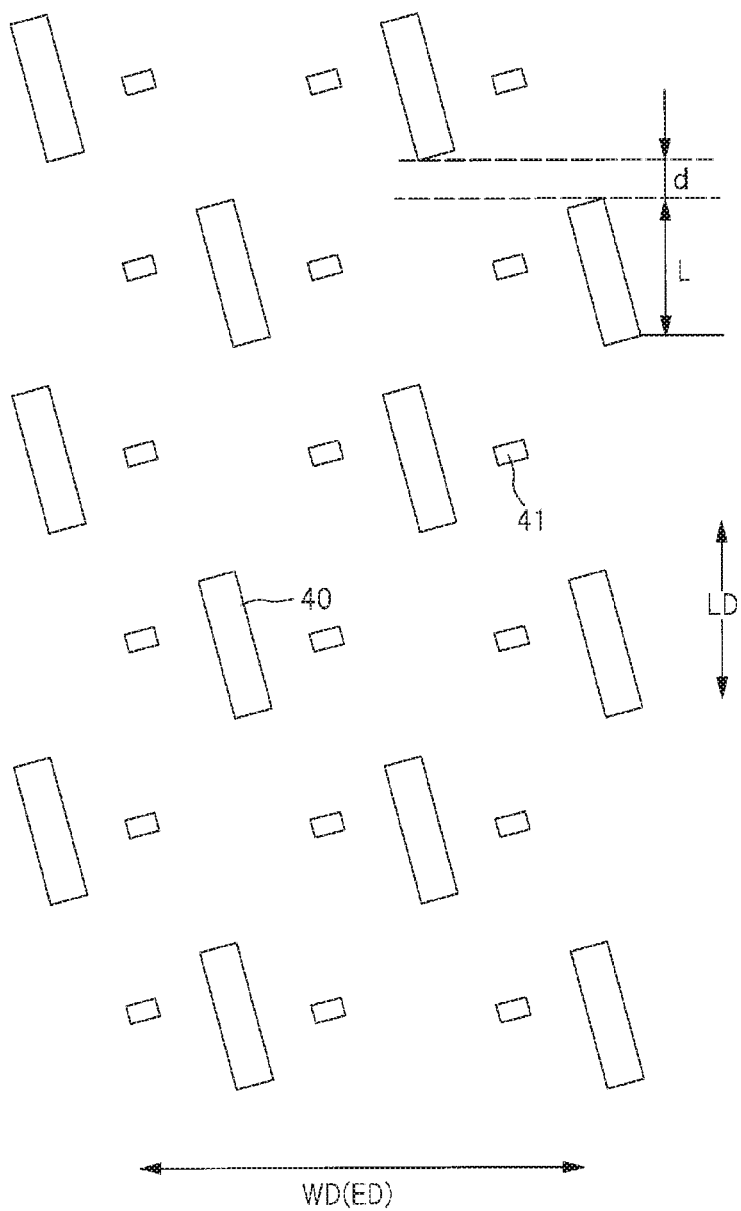

[FIG.19]
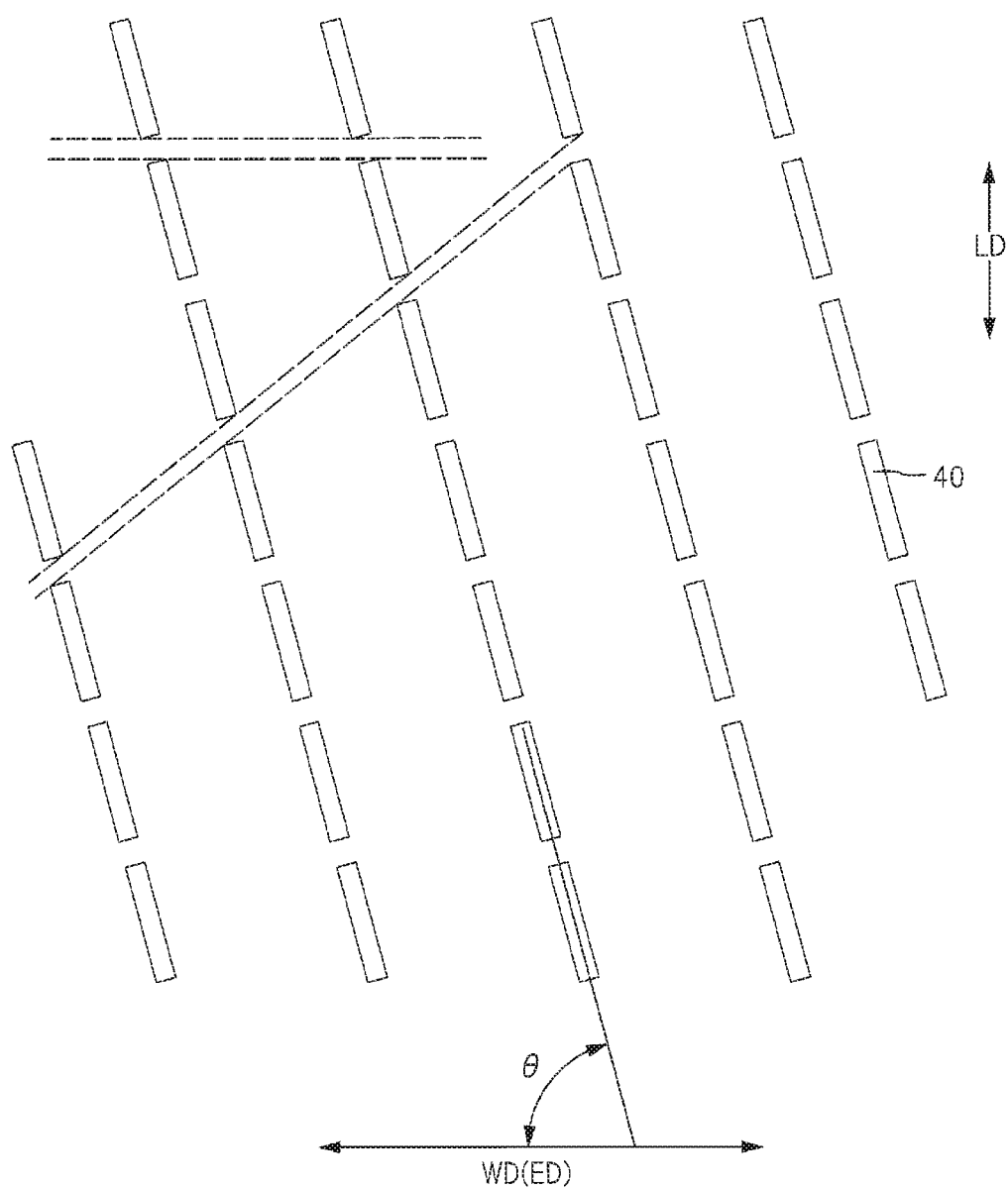

[FIG.20]
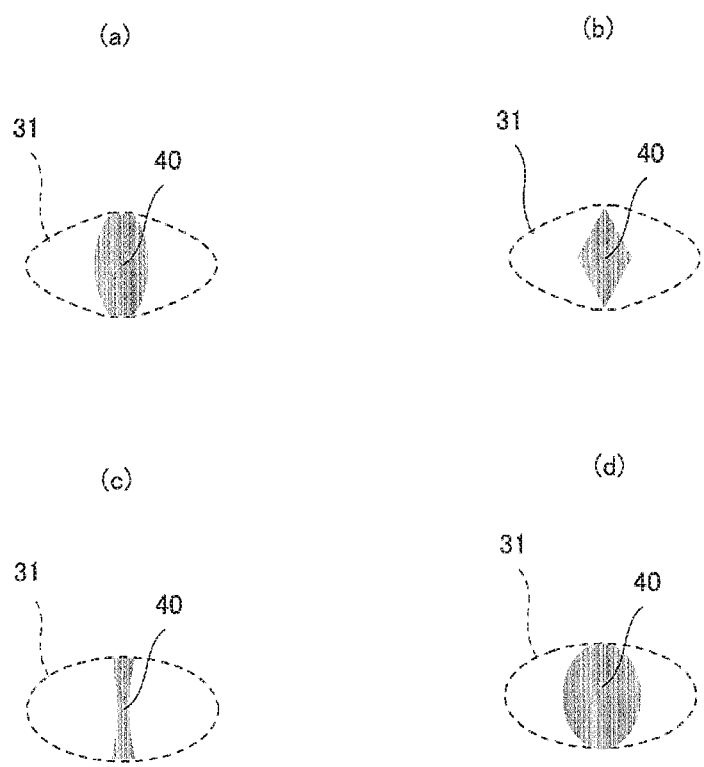

[FIG.21]
(a)
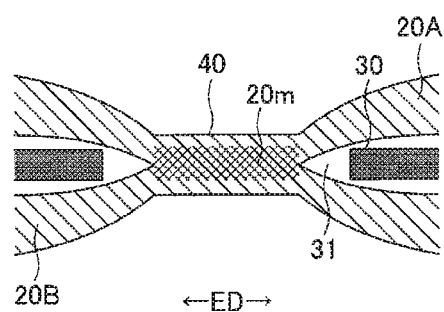
(b)
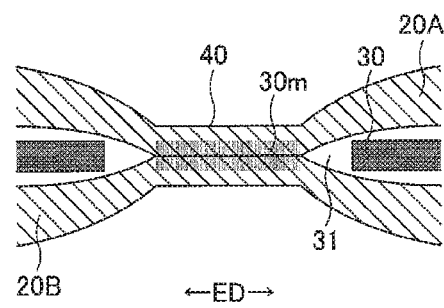
(c)
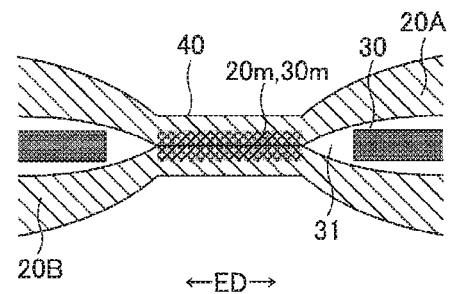

[FIG.22]
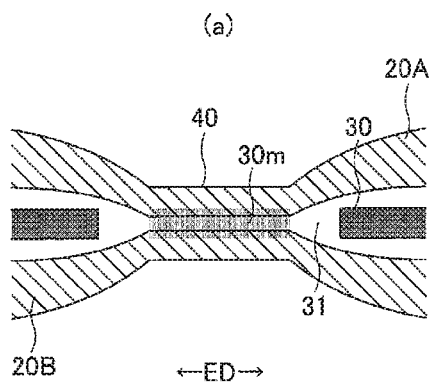
(a)
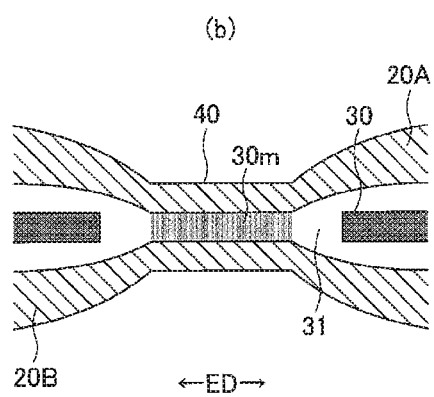
(b)
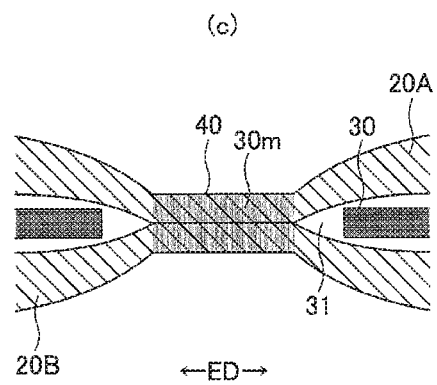
(c)

[FIG.23]
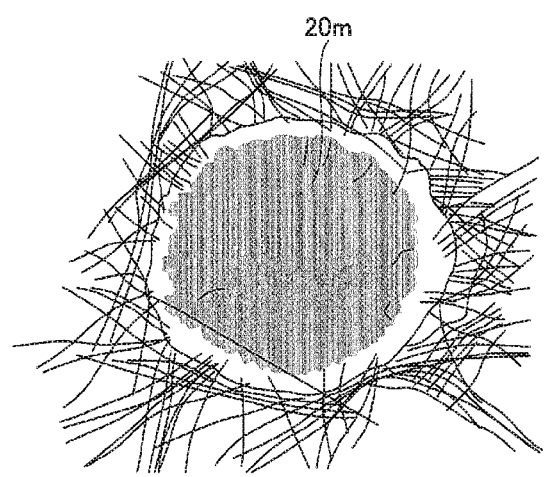
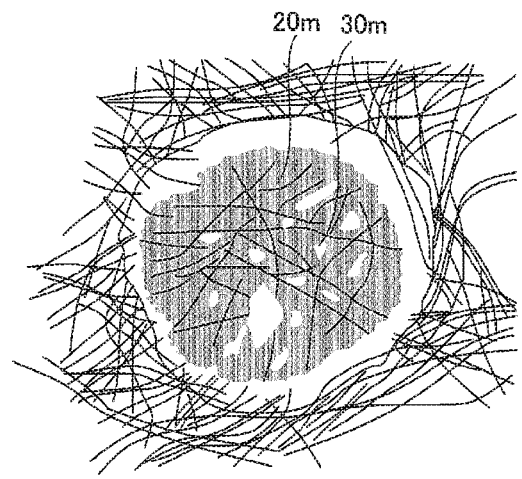
(b)

[FIG.24]
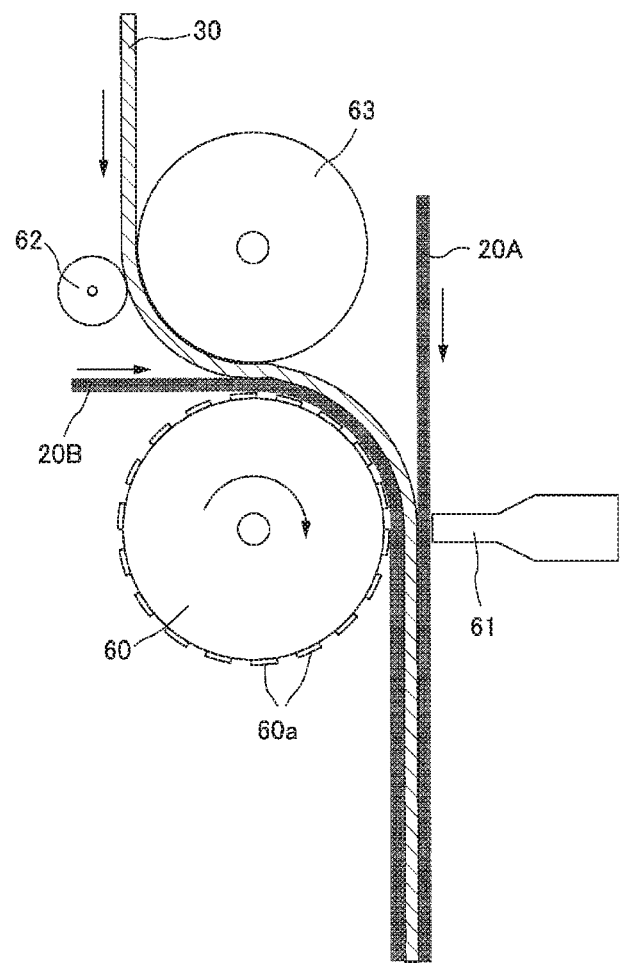

[FIG.25]
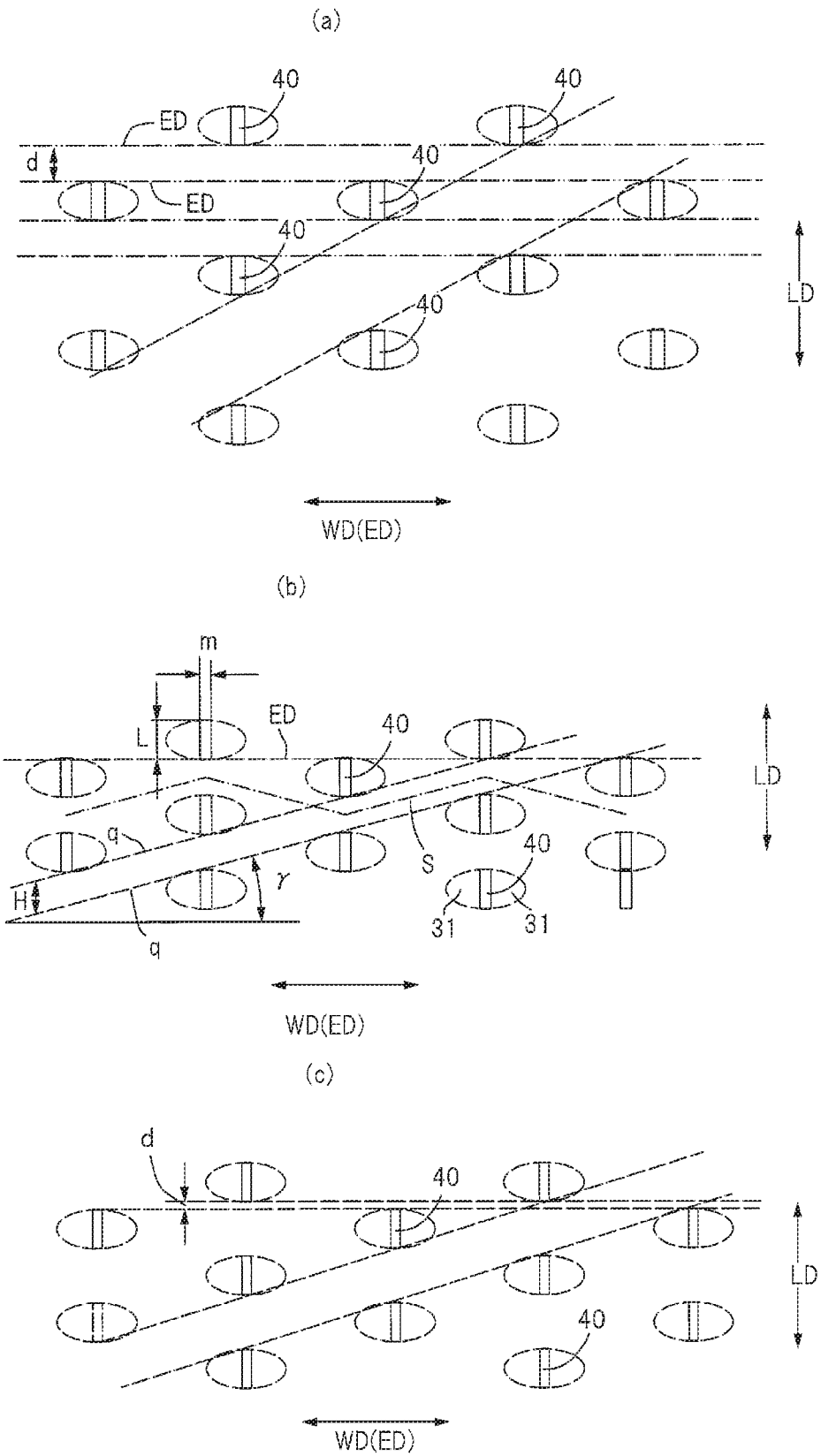

ELASTIC MEMBER AND DISPOSABLE WEARING ARTICLE INCLUDING ELASTIC MEMBER

CROSS-REFERENCE TO RELATED APPLICATIONS

This application is the U.S. national stage application of International Application PCT/JP2018/035312, filed Sep. 25, 2018, which international application was published on Apr. 4, 2019, as International Publication WO 2019/065575 in the Japanese language. The International Application claims priority of Japanese Patent Application Nos. 2017-187179, filed Sep. 27, 2017 and 2018-051155, filed Mar. 19, 2018. The international application and Japanese application are all incorporated herein by reference, in entirety.

TECHNICAL FIELD

The present invention relates to an elastic member having a stretchable structure in which an elastic sheet such as an elastic film is interposed between a first sheet layer and a second sheet layer, and a disposable wearing article including this elastic member.

BACKGROUND ART

In a disposable wearing article such as a disposable diaper, to improve fitting to a body surface, it is common to impart elasticity to an appropriate place such as around legs or around a waist. As a method of imparting elasticity, a method of attaching an elongated elastic member such as rubber thread in a state of being stretched in a longitudinal direction has been widely adopted. However, in the case of imparting elasticity at a certain width, a mode in which rubber threads are fixed in a state of being arranged side by side with an interval in the width has been adopted. In addition, as a method of obtaining an excellent surface fitting, a method of attaching an elastic sheet in a state of being stretched in a direction of imparting elasticity has been proposed. (For example, see Patent Literature 1).

The elastic member including the elastic sheet is obtained when an elastic film is stacked between a first sheet layer and a second sheet layer, and, in a state in which the elastic film is stretched in a stretchable direction, the first sheet layer and the second sheet layer are bonded by a plurality of dotted sheet joined portions arranged at intervals in the stretchable direction and a direction orthogonal thereto through joint holes formed in the elastic film. Further, in this elastic member, in a natural length state, as the elastic sheet contracts between the sheet joined portions, the intervals between the sheet joined portions decrease, and pleats are formed to extend in a direction intersecting the stretchable direction between the sheet joined portions in the first sheet layer and the second sheet layer. On the contrary, during stretching, as the elastic sheet stretches between the sheet joined portions, the intervals between the sheet joined portions and the pleats in the first sheet layer and the second sheet layer widen, and elastic stretching is allowed up to a fully unfolded state of the first sheet layer and the second sheet layer.

A stretchable region by this elastic sheet is advantageous in that surface fitting is excellent, there is no bonding between the first sheet layer and the second sheet layer, and the elastic sheet, the structure is significantly flexible due to extremely little bonding between the first sheet layer and the second sheet layer, and the joint holes of the elastic sheet also contribute to improvement in air permeability.

In addition to air permeability of the first sheet layer and the second sheet layer, joint holes of the elastic sheet greatly contribute to improvement of air permeability.

In order to ensure air permeability, a product is designed so that the joint holes open in a normal use state of the wearer. However, in the case of a wearer having a thin body shape, the joint holes tend to be closed during wearing. As a result, air permeability may not be sufficiently ensured.

CITATION LIST

Patent Literature

Patent Literature 1: JP 5967736 B2
Patent Literature 2: JP 2015-204982 A

SUMMARY OF INVENTION

Technical Problem

Therefore, a main problem of the invention is to prevent joint holes from being excessively closed and air permeability from being lowered.

Solution to Problem

An elastic member solving the above problem has an elastic sheet stretchable structure in which an elastic sheet is interposed between a first sheet layer and a second sheet layer and the first sheet layer and the second sheet layer are bonded through joint holes penetrating the elastic sheet or via the elastic sheet at a plurality of sheet joined portions arranged at intervals, in which a region having the elastic sheet stretchable structure includes a stretchable region that contracts in a stretchable direction by contraction of the elastic sheet and is extensible in the stretchable direction, joined portions are separately formed in the stretchable direction and an orthogonal direction orthogonal thereto in the stretchable region, a joined portion group of the stretchable region is in a relationship of intersecting a stretchable direction line at respective positions in the orthogonal direction or in a relationship of not intersecting the stretchable direction line at a separation width of 0.5 mm or less in the orthogonal direction of the stretchable direction line, and the joined portion group is in a relationship of not intersecting an oblique line at a predetermined separation width in the orthogonal direction in an oblique line group of oblique lines in the orthogonal direction intersecting the stretchable direction line within an angle range of 45 degrees or less.

It is possible to adopt an aspect in which the joined portions are aligned along an oblique line intersecting the stretchable direction line within an angle range of 45 degrees or less.

Provided is an underpants-type disposable wearing article including an integrated outer member covering from a front body to a back body or outer members separately provided for the front body and the back body, an inner member attached to an intermediate portion of the outer member in a width direction to extend to both front and back sides of a crotch portion, side seal portions in which both side portions of the outer member in the front body and both side portions of the outer member in the back body are bonded to each other, and a waist opening and a pair of right and left leg openings, in which the outer member in at least one of the front body and the back body is an elastic member having the elastic sheet stretchable structure according to the above aspect over a range in the width direction corresponding to a space between the side seal portions at least in a partial range in a front-back direction so that an stretchable direction of a stretchable region thereof corresponds to the width direction.

Advantageous Effects of Invention

According to the invention, it is possible to prevent joint holes from being excessively closed and air permeability from being lowered.

BRIEF DESCRIPTION OF DRAWINGS

FIG. 1 is a plan view (internal surface side) of an underpants-type disposable diaper in an unfolded state.

FIG. 2 is a plan view (external surface side) of the underpants-type disposable diaper in the unfolded state.

FIG. 3 is a plan view illustrating only a main part of the underpants-type disposable diaper in the unfolded state.

FIG. 4(a) is a cross-sectional view taken along C-C line of FIG. 1, and FIG. 4(b) is a cross-sectional view taken along E-E line of FIG. 1.

FIG. 5 is a cross-sectional view taken along A-A line of FIG. 1.

FIG. 6 is a cross-sectional view taken along B-B line of FIG. 1.

FIG. 7 is a plan view (internal surface side) of a main part of a stretchable region in the underpants-type disposable diaper in the unfolded state.

FIG. 8(a) is a cross-sectional view corresponding to C-C line of FIG. 1, and FIG. 8(b) is a cross-sectional view corresponding to E-E line of FIG. 1.

FIG. 9 is a plan view and a cross-sectional view illustrating joined portion arrangement disclosed by Patent Literature 1.

FIG. 10 is a plan view illustrating joined portion arrangement disclosed by Patent Literature 2.

FIG. 11 illustrates a first example of joined portion arrangement of the invention, in which FIG. 11(a) is a plan view and FIG. 11(b) is a cross-sectional view taken along B-B line.

FIG. 12 illustrates a second example of joined portion arrangement of the invention, in which FIG. 12(a) is a plan view and FIG. 12(b) is a cross-sectional view taken along B-B line.

FIG. 13 is a plan view illustrating a third example of joined portion arrangement of the invention.

FIG. 14 is a plan view illustrating a fourth example of joined portion arrangement of the invention.

FIG. 15 is a plan view illustrating a fifth example of joined portion arrangement of the invention.

FIG. 16 is a plan view illustrating a sixth example of joined portion arrangement of the invention.

FIG. 17 is a plan view illustrating a seventh example of joined portion arrangement of the invention.

FIG. 18 is a plan view illustrating an eighth example of joined portion arrangement of the invention.

FIG. 19 is a plan view illustrating a ninth example of joined portion arrangement of the invention.

FIG. 20 is an explanatory diagram of a shape example of joined portions.

FIG. 21 is a cross-sectional view illustrating a bonding mode example in joined portions of the invention.

FIG. 22 is a cross-sectional view illustrating a bonding mode example in joined portions of the invention.

FIG. 23 is a plan view illustrating the bonding mode example.

FIG. 24 is a schematic view of an ultrasonic sealing device for manufacturing an elastic member.

FIG. 25(a) is a joined portion arrangement example of a conventional example, FIG. 25(b) is a joined portion arrangement example of an example of the invention, and FIG. 25(c) is an explanatory diagram of the joined portion arrangement example of the example of the invention.

DESCRIPTION OF EMBODIMENTS

Hereinafter, an embodiment of the invention will be described in detail with reference to accompanying drawings. Incidentally, a dotted pattern portion in a cross-sectional view illustrates bonding means such as a hotmelt adhesive.

FIG. 1 to FIG. 6 illustrate an underpants-type disposable diaper (hereinafter also simply referred to as a diaper) as an example of a disposable wearing article of the invention. Reference character WD (ED) denotes a stretchable direction ED of a stretchable region in a width direction of the diaper. Reference character LD denotes a front-back direction of the diaper and a direction orthogonal to the stretchable direction ED.

The underpants-type disposable diaper includes an outer member 20 forming a front body F and a back body B, and an inner member 10 fixed to and integrated with an inner surface of the outer member 20, and the inner member 10 is formed by interposing an absorbent body 13 between a liquid pervious top sheet 11 and a liquid impervious sheet 12. In manufacturing, after a back surface of the inner member 10 is bonded to the inner surface (upper surface) of the outer member 20 by bonding means such as a hotmelt adhesive, the inner member 10 and the outer member 20 are folded at a center in the front-back direction LD (longitudinal direction) corresponding to a boundary between the front body F and the back body B, and both side portions thereof are bonded to each other by thermal welding or the hotmelt adhesive to form side seal portions 21, thereby obtaining the underpants-type disposable diaper in which a waist opening and a pair of right and left leg openings are formed.

(Structure Example of Inner Member)

As illustrated in FIG. 4 to FIG. 6, the inner member 10 has a structure in which the absorbent body 13 is interposed between the liquid pervious top sheet 11 and the liquid impervious sheet 12 made of polyethylene, etc. and absorbs and holds excretion fluid passing through the top sheet 11. A planar shape of the inner member 10 is not particularly limited. However, a substantially rectangular shape is generally adopted as illustrated in FIG. 1.

As the liquid pervious top sheet 11 that covers the front surface side (skin side) of the absorbent body 13, a perforated or non-perforated nonwoven fabric, a porous plastic sheet, etc. is preferably used. As a material fiber constituting the nonwoven fabric, it is possible to adopt a regenerated fiber such as rayon and cupra or a natural fiber such as cotton in addition to a polyolefin-based synthetic fiber such as polyethylene or polypropylene, a polyester-based synthetic fiber, a polyamide-based synthetic fiber, etc., and it is possible to use a nonwoven fabric obtained by an appropriate processing method such as a spunlace method, a spunbond method, a thermal bond method, a meltblown method, a needle punch method, etc. Among these processing methods, the spunlace method is excellent in terms of flexibility and drape, and the thermal bond method is excellent in terms of being bulky and soft. When a large number of through-holes are formed in the liquid pervious top sheet 11, urine, etc. is quickly absorbed, and a dry touch property is excellent. The liquid pervious top sheet 11 is wound around a side edge portion of the absorbent body 13 and extends to a back surface side of the absorbent body 13.

As the liquid impervious sheet 12 that covers the back surface side (non-skin contact side) of the absorbent body 13, a liquid impervious plastic sheet such as polyethylene or polypropylene is used. However, in recent years, a sheet having a moisture penetration property is preferably used from a viewpoint of preventing stuffiness. For example, this water-impervious and moisture-permeable sheet is a microporous sheet obtained by melt-kneading an inorganic filler in an olefin resin such as polyethylene or polypropylene to form a sheet, and then stretching the sheet in a uniaxial or biaxial direction.

As the absorbent body 13, it is possible to use a known one, for example, a pulp fiber stack, an assembly of filaments of cellulose acetate, etc., or a nonwoven fabric-based body mixed with a high-absorbent polymer as necessary and fixed. To hold the shape and the polymer, the absorbent body 13 can be wrapped in a package sheet 14 having a liquid pervious and liquid retaining property such as crepe paper as necessary.

The absorbent body 13 is formed into a substantially hourglass shape having a narrower portion 13N narrower than both front and back sides at a crotch portion. A size of the narrower portion 13N can be determined as appropriate. A length of the narrower portion 13N in the front-back direction can be set to about 20 to 50% of a maximum length of the diaper, and a width of a narrowest portion thereof can be set to about 40 to 60% of a maximum width of the absorbent body 13. In the case of having such a narrower portion 13N, when the planar shape of the inner member 10 is substantially rectangular, non-absorbent body side portions 17 not having the absorbent body 13 are formed at a portion corresponding to the narrower portion 13N of the absorbent body 13 in the inner member 10.

The liquid impervious sheet 12 is folded back to the back surface side on both sides of the absorbent body 13 in the width direction together with the liquid pervious top sheet 11. As this liquid impervious sheet 12, it is desirable to use an opaque sheet so that brown color of excreta or urine is not seen. As opacification, a pigment or a filler such as calcium carbonate, titanium oxide, zinc oxide, white carbon, clay, talc, or barium sulfate added to plastic and formed into a film is preferably used.

Three-dimensional gathers 90 fit around the legs are formed on both side portions of the inner member 10. As illustrated in FIG. 5 and FIG. 6, each of the three-dimensional gathers 90 includes a fixed portion 91 fixed to a side portion of the back surface of the inner member 10, a main unit section 92 extending from the fixed portion 91 up to a side portion of the front surface of the inner member 10 through a side of the inner member 10, a fallen portion 93 formed by front and back end portions of the main unit section 92 fixed to the side portion of the front surface of the inner member 10 (top sheet 11 in the illustrated embodiment) in a fallen state, and a free portion 94 formed between parts of the fallen portion 93 which are not fixed. Each of these portions is formed of a gather sheet 95 that is a duplicate sheet obtained by folding a sheet such as a nonwoven fabric. The gather sheet 95 is attached over the entire inner member 10 in the front-back direction, the fallen portion 93 is provided on the front side and the back side of each of the non-absorbent body side portions 17, and the free portion 94 extends to both the front and back sides of the non-absorbent body side portion 17. In addition, between the double gather sheets 95, elongated gather elastic members 96 are disposed at tip portions of the free portion. As illustrated in FIG. 5, the gather elastic members 96 are for raising the free portion 94 by an elastic contraction force in a product state.

In an embodiment illustrated in FIG. 5 and FIG. 6, in portions other than fallen non-stretchable portions 97, the gather elastic members 96 are attached and fixed to the gather sheets 95 through a hotmelt adhesive at positions of the gather elastic members 96, and facing surfaces of the gather sheets 95 are bonded to each other. However, in the fallen non-stretchable portions 97, the hotmelt adhesive is not present at the positions of the gather elastic members 96. Therefore, the gather elastic members 96 and the gather sheets 95 are not attached to each other, and the facing surfaces of the gather sheets 95 are not bonded to each other at positions having the gather elastic members 96.

Each of the three-dimensional gathers 90 illustrated in FIG. 5 and FIG. 6 has a form in which the main unit section 92 is not folded back.

As the gather elastic members 96, it is possible to use normally used materials such as polystyrene-based rubber, polyolefin-based rubber, polyurethane-based rubber, polyester-based rubber, polyurethane, polyethylene, polystyrene, styrene-butadiene copolymer, silicone, polyester, etc. In addition, to make it difficult to see from the outside, it is preferable that a fineness is set to 925 dtex or less, a tension is set to 150 to 350%, and an interval is set to 7.0 mm or less. Incidentally, as the gather elastic members 96, it is possible to use a tape-like member having a certain width in addition to a thread-like member as in the illustrated embodiment.

As a material fiber constituting the gather sheets 95 described above, similarly to the liquid pervious top sheet 11, it is possible to adopt a recycled fiber such as rayon or cupra or a natural fiber such as cotton in addition to a polyolefin-based synthetic fiber such as polyethylene or polypropylene, a polyester-based synthetic fiber, a polyamide-based synthetic fiber, etc., and it is possible to use a nonwoven fabric obtained by an appropriate processing method such as a spunbond method, a thermal bond method, a meltblown method, a needle punch method, etc. However, in particular, in order to prevent stuffiness, it is preferable to use a nonwoven fabric that suppresses a basis weight and has excellent air permeability. Further, with regard to the gather sheets 95, to prevent passage of urine, etc., prevent a rash, and enhance a feel to a skin (dry feeling), it is preferable to use a water repellent nonwoven fabric coated with a silicone-based, paraffin metal-based, or alkylchromic chloride-based water repellent agent, etc.

As illustrated in FIG. 3 to FIG. 6, the back surface of the inner member 10 is bonded to the inner surface of the outer member 20 by a hotmelt adhesive, etc. in an inner/outer fixing region 10B (shaded region). The inner/outer fixing region 10B may be determined as appropriate and may correspond to almost the entire inner member 10 in a width direction WD. However, it is preferable that both ends in the width direction are not fixed to the outer member 20.

(Structure Example of Outer Member)

The outer member 20 extends to the outside of side edges of the absorbent body 13. Referring to the outer member 20, as in the illustrated embodiment, in a crotch portion, side edges of the outer member 20 may be located on a central side of side edges of the inner member 10 in the width direction or located on an outer side thereof in the width direction. In addition, the outer member 20 includes lower torso portions T which are front-back direction ranges corresponding to the side seal portions 21 and an intermediate portion L which is a front-back direction range between the lower torso portion T of the front body F and the lower torso portion T of the back body B.

Further, the outer member 20 of the illustrated embodiment has an elastic sheet stretchable structure 20X in which an elastic sheet, for example, an elastic film 30 is interposed between the first sheet layer 20A and the second sheet layer 20B as illustrated in FIG. 2 and FIG. 4 to FIG. 6 except for a middle of the intermediate portion L in the front-back direction and the first sheet layer 20A and the second sheet layer 20B are bonded through joint holes 31 penetrating the elastic film 30 at a plurality of sheet joined portions 40 arranged at intervals as illustrated in FIG. 9.

In an embodiment of application to the diaper, a stretchable direction ED of the elastic sheet (the elastic film 30 in an example of FIG. 9) is regarded as the width direction WD of the diaper.

The first sheet layer 20A and the second sheet layer 20B may be indirectly bonded through the elastic film 30 instead of through the joint holes 31 of the elastic film 30. A planar shape of the outer member 20 is formed by concave around-leg lines 29 so that both side edges of the intermediate portion L in the width direction form leg openings, respectively, and has a shape similar to an hourglass as a whole. The outer member 20 may be formed separately in the front body F and the back body B, and both bodies may be disposed to be separated in the front-back direction LD of the diaper at the crotch portion.

An embodiment illustrated in FIG. 1 and FIG. 2 is an embodiment in which the elastic sheet stretchable structure 20X extends up to waist end portions 23. However, if necessary, for example, if tightening of the waist end portions 23 is insufficient when the elastic sheet stretchable structure 20X is used for the waist end portions 23, the stretchable structure may be provided by conventional elongated waist portion elastic members 24 without providing the elastic sheet stretchable structure 20X in the waist end portions 23 as illustrated in FIG. 7 and FIG. 8. The waist portion elastic members 24 are elongated elastic members such as a plurality of rubber threads disposed at intervals in the front-back direction LD, and apply a stretching force to tighten a waist of a body. The waist portion elastic members 24 are not disposed substantially in a bundle at close intervals, and three or more waist portion elastic members 24, preferably five or more waist portion elastic members 24 are disposed at intervals of about 3 to 8 mm in the front-back direction to form a predetermined stretchable zone. A stretch rate the waist portion elastic members 24 at the time of fixing can be determined as appropriate, and may be set to about 230 to 320% for a normal adult. As the waist portion elastic members 24, rubber threads are used in the illustrated example. However, other elongated elastic members such as flat rubber may be used. Although not illustrated, the elastic film 30 may be provided at the waist end portions 23, and the elongated waist portion elastic members 24 may be provided at positions overlapping the elastic film 30, so that a stretchable structure using both elastic members can be provided.

In addition, in the illustrated embodiment, the elongated elastic members extending along leg openings are not provided at edge portions of the leg openings in the outer member 20. However, the elongated elastic members may be provided at positions overlapping the elastic film 30 at the edge portions or instead of the elastic film 30 at the edge portions.

As other embodiments, although not illustrated, appropriate modifications can be made. For example, the elastic sheet stretchable structure 20X may not be provided in the intermediate portion L between the lower torso portion T of the front body F and the lower torso portion T of the back body B, the elastic sheet stretchable structure 20X may be continuously provided in the front-back direction LD from the inside of the lower torso portion T of the front body F to the inside of the lower torso portion T of the back body B via the intermediate portion L, or the elastic sheet stretchable structure 20X may be provided only in one of the front body F and the back body B.

Embodiment of Joined Portions

The invention has a characteristic in arrangement of the joined portions with respect to a stretching force. To clarify this characteristic, arrangement of joined portions of a conventional example will be described in detail.

FIG. 9 is illustrated as a representative example for Patent Literature 1.

In more detail, a group of the joined portions 40 has staggered arrangement, the joined portions 40 are elongated in a direction orthogonal to the stretchable direction and in line symmetry with respect to a center line passing through a center in the stretchable direction (lateral symmetry in FIG. 9(a)), a width 40x of each of the joined portions 40 in the stretchable direction is preferably set to 0.2 to 0.4 mm, an interval d1 between the joined portions 40 arranged in the stretchable direction is set to 3 to 12.9 mm, more preferably 5 to 6.4 mm, and an interval d2 between the joined portions 40 arranged in the direction orthogonal to the stretchable direction is set to 2 to 10.5 mm, more preferably 2.3 to 4.6 mm.

As described above, the joined portions 40 having the remarkably narrow width 40x in the stretchable direction are arranged in a staggered manner at the separation interval d1 which is somewhat wide in the stretchable direction, the contraction force of the elastic film 30 directly acts on each of the joined portions 40, and arrangement and intervals of the respective joined portions 40 are firmly maintained at the positions of the joint holes 31 of the elastic film 30. As a result, flexibility is unlikely to decrease. In addition, pleats 25f extend almost straight along the direction orthogonal to the stretchable direction, and each of the joined portions 40 is hidden between the pleat 25f and the pleat 25f and are not noticeable. Therefore, the elastic sheet stretchable structure 20X having an appearance closer to that of cloth is obtained while suppressing a decrease in flexibility.

On the other hand, when the joined portion 40 has a circular shape even though arrangement of the joined portions 40 corresponds to staggered arrangement, the joined portion 40 is clearly visible between the pleat 25f and the pleat 25f in wrinkles, and the pleats 25f extend in the direction orthogonal to the stretchable direction by largely going around the joined portions 40. Thus, wavy pleats 25f are formed as a whole, and there is a tendency that a cloth-like appearance may not be obtained.

From such a viewpoint, it is desirable that the shape of the joined portion 40 is elongated in the direction orthogonal to the stretchable direction. However, when a maximum length of the joined portion 40 in the direction orthogonal to the stretchable direction is excessively short or excessively long, there is concern that linearity of the pleats 25f may be lowered or flexibility may be lowered. Therefore, even though these dimensions can be determined as appropriate, it is preferable that a length 40y of the joined portion 40 in the direction orthogonal to the stretchable direction is 0.4 to 3.2 mm, particularly 0.7 to 1.4 mm.

On the other hand, in Patent Literature 2, arrangement of joined portions of the elastic film (illustrated as slightly vertically long rectangles) is staggered arrangement in both the two examples illustrated in FIGS. 10(a) and 10(b), and small circular sub-joined portions are disposed between rectangular main joined portions in the example of FIG. 10(b). The example of FIG. 10(b) is based on an idea of staggered arrangement.

Further, arrangement and dimensions of the respective joined portions are preferably in the dimension ranges (unit is mm) described in FIG. 10 mainly from viewpoints of appearance, texture, air permeability, etc.

Both inventions of Patent Literatures 1 and 2 disclose vertically long joined portions and staggered arrangement.

However, in the conventional example, since the separation interval between the joined portions of the elastic film in the direction orthogonal to the stretchable direction (reference character C in FIG. 10(a)) is set to be as large as 0.3 mm, the stretching stress in the stretchable direction is high. For example, in the case of application to an underpants type disposable diaper, not a few wearers feel that the wearers are excessively strongly tightened (in the width direction).

Here, in Patent Literature 2, it is considered preferable when a joined portion length B illustrated in FIG. 10 is 0.3 to 0.7 mm, and a separation interval H is 0.6 to 1.4 mm.

On the other hand, the applicant has found that when the separation interval d between the joined portions of the elastic film in the direction orthogonal to the stretchable direction WD (ED) (up-down direction in the figure: direction of reference character LD) is set to be small as illustrated in FIG. 11, the stretching stress in the stretchable direction can be decreased, and thus the diaper can be gently fit to the wearer by a weak tightening force in the case of application to the underpants type disposable diaper.

A reason therefor is considered to be as follows. While the joined portions open in the width direction to become the joint holes 31 as illustrated in FIG. 9 merely by applying a small stretching force in the width direction (stretchable direction of the elastic film) from the outside. On the other hand, since the joined portions are not present in a separation interval region orthogonal to the stretchable direction between the joined portions, even when stretched in the width direction, the stretching stress of the elastic film acts as the contraction force without change to tighten the wearer.

An embodiment illustrated in FIG. 11 can easily fit the diaper to the wearer, and has an advantage that air permeability is excellent since a ratio of an area occupied by the joined portions and a ratio of an area occupied by the joint holes in a use state of being stretched in the width direction increase.

The embodiment illustrated in FIG. 11 has an advantage that the diaper can be easily fit to the wearer. However, it is desirable to apply a weaker contraction force in some cases.

Further, a diaper product provider generally determines the contraction force of the diaper on the wearer by setting a person having an intermediate body shape within a certain body shape (size around a waist) group.

The size around the waist greatly varies between individuals, and there is a desire for a diaper product in which the contraction force of the diaper on the wearer does not change much between a large person having a fat waist and a small person having a thin waist as much as possible.

The present inventor is not aware of an effective solution to such a problem. However, the inventor accidentally found a gradual solution.

This solution is described below with reference to FIG. 25.

That is, the above problem is solved when the joined portions 40 are formed separately in the stretchable direction ED and the orthogonal direction LD orthogonal thereto in the stretchable region, a group of the joined portions 40, 40 . . . in the stretchable region is in a relationship intersecting a line in the stretchable direction ED at respective positions in the orthogonal direction LD as in FIG. 25(b), or in a relationship of not intersecting the line in the stretchable direction ED at a separation width of 0.5 mm or less in the orthogonal direction LD of the line in the stretchable direction ED as in FIG. 25(c), and the joined portion group is in a relationship of not intersecting an oblique line at a predetermined separation width in the orthogonal direction LD in an oblique line group of oblique lines q in the orthogonal direction LD intersecting the stretchable direction line ED within an angle γ range of 45 degrees or less (that is, an oblique line group between oblique lines q and q of FIG. 25(b)).

A reason why this solution does not give an excessive contraction force to the wearer may not be clear. However, it is presumed that the reason is that the following phenomenon occurs.

It seems that stretching in the stretchable direction may not occur in the case of a relationship of intersecting the line in the stretchable direction ED at respective positions in the orthogonal direction LD as in FIG. 25(b) or a relationship of not intersecting the line in the stretchable direction ED at a separation width d of 0.5 mm or less in the orthogonal direction LD of the line in the stretchable direction ED as in FIG. 25(c).

However, a force in the stretchable direction in the case of spreading in the stretchable direction during wearing propagates while detouring as in FIG. 25(b) (a propagation path is indicated by reference character S). The reason for indicating this propagation path S is that when the elastic sheet is, for example, an elastomer elastic film, the sheet stretches and contracts in the orthogonal direction in addition to the width direction. Thus, it is found that stretching in the stretchable direction occurs while forming the joint holes 31 and 31 on both sides of the joined portion 40 in the width direction.

In general, when the elastic sheet is stretched and then a stretching force thereof is released, the elastic sheet does not return to an original length and returns to a length obtained by subtracting a strain. For example, assuming that an elastic sheet having a natural length of 50 mm has a length of 70 mm when the elastic sheet is stretched 3.5 times to 175 mm and a stretching force is released, there is a strain of 20 mm, and a strain ratio E % is (70−50)×100/50=40%.

When a further examination is carried out considering this fact, stretching in the stretchable direction occurs while forming the joint holes 31 and 31 on both sides of the joined portion 40 in the width direction in the unfolded state of the diaper in the width direction. That is, the elastic sheet is deformed by openings of the joint holes 31 and 31 on both sides of the joined portion 40 in the width direction. It is understood that a deformed portion has a reduced contraction force.

As described above, when an unfolding force of the diaper is released, the elastic sheet contracts in the width direction while shortening an opening width (opening length) of the joint holes 31 and 31 by the contraction force of the elastic sheet. In this case, when the separation width d is large (referred to as a "contrast example"), the elastic sheet is not deformed in a separation width d region, and thus an amount (length) of contraction in the width direction is large. For example, in a thin person, contraction occurs until the joint holes 31 and 31 are closed. In this case, initially aimed air permeability from the openings of the joint holes 31 and 31 is insufficiently ensured.

On the other hand, as in the invention, as a result of a state in which the elastic sheet is deformed (in a sense a state in which the elastic sheet is damaged) due to the openings of the joint holes 31 and 31 in all or almost all part in the orthogonal direction since the separation width d is small or zero, the opening width (opening length) of the opened joint holes 31 and 31 is short and the ratio is small in a case in which the stretching force in the width direction is released, so that ensuring of the initially aimed air permeability from the openings of the joint holes 31 and 31 is not excessively lowered.

Moreover, since the contraction force in the width direction is smaller than that of the "contrast example", the wearer is not excessively pressed.

Incidentally, for example, to cause stretching and contraction in the width direction in the propagation path S, it is necessary to have a relationship in which the group of the joined portions 40, 40 . . . does not intersect the oblique line at a predetermined separation width H in the orthogonal direction in an oblique line group of oblique lines q and q in the orthogonal direction intersecting the stretchable direction ED within an angle γ range less than or equal to 45 degrees as in FIG. 25(*b*).

Here, for example, as in FIG. 17, the angle γ less than or equal to 45 degrees with respect to the line in the stretchable direction ED is defined as an opening angle between the line in the stretchable direction ED and the oblique line q even in the case of an oblique line from the upper left to the lower right.

The separation width H along the orthogonal direction LD is desirably 0.2 to 10 mm, more desirably 0.2 to 5.0 mm, and particularly desirably 0.6 to 3.0 mm.

The opening angle γ between the stretchable direction ED and the oblique line is more preferably 30 degrees or less, and particularly preferably 15 degrees or less.

The joined portion 40 is formed to have a width of 0.3 to 10.0 mm, preferably 0.5 to 5.0 mm, particularly preferably 0.7 to 3.5 mm in the stretchable direction.

The joined portion 40 is formed to have a length L of 0.3 to 7.0 mm, preferably 0.5 to 5.0 mm, particularly preferably 0.7 to 2.5 mm with respect to the orthogonal direction LD.

In addition, the row of the first joined portions 40, 40 . . . is formed so that a formation pitch S0 with respect to the stretchable direction ED (WD) is 2.0 to 20.0 mm, preferably 3.0 to 15.0 mm, particularly preferably 4.0 to 10.0 mm.

Various modifications of the invention are present under the above basic mode, and thus representative embodiments will be shown below.

First Example

However, in a usage mode in a product of the embodiment illustrated in FIG. 11(*a*), a wrinkle along an orthogonal direction LD is formed in a separation region between a row of joined portions 40, 40 . . . along the orthogonal direction LD and a row of joined portions 40, 40 . . . separated from and adjacent to the row in the stretchable direction WD (ED: width direction). As illustrated in FIG. 11(*b*), this wrinkle 25F simply has a uniform mountain shape. That is, this shape is shown in Patent Literature 1 and different from a cross section illustrated in FIG. 9(*c*).

Second Example

An elastic member according to a first example illustrated in FIG. 12 has an elastic sheet stretchable structure in which an elastic sheet is interposed between a first sheet layer having air permeability and a second sheet layer having air permeability, and the first sheet layer and the second sheet layer are bonded through joint holes penetrating the elastic sheet or via the elastic sheet at a plurality of sheet joined portions arranged at intervals.

A stretchable region exhibiting the elastic sheet stretchable structure can be stretched in the stretchable direction by a contraction force of the elastic sheet.

The joined portions have second joined portions 41, 41 . . . in addition to first joined portions 40, 40 . . . .

The first joined portions 40, 40 . . . are arranged at intervals along the orthogonal direction LD to form a first joined portion row.

As will be described later with reference to FIG. 19, for example, it is desirable that the row of the first joined portions 40, 40 . . . is inclined to intersect the stretchable direction ED at an angle θ within a range of 30 degrees to 150 degrees (therefore not including 90 degrees), and it is more desirable that the row is inclined within a range of 45 degrees to 135 degrees (not including 90 degrees) without extending along the orthogonal direction LD.

The second example is an example in which the angle θ of intersection, not inclination, is 90 degrees.

The first joined portion 40 is formed to have a length L of 0.3 to 7.0 mm, preferably 0.5 to 5.0 mm, particularly preferably 0.7 to 2.5 mm with respect to the orthogonal direction LD.

In addition, the row of the first joined portions 40, 40 . . . is formed so that a formation pitch S0 with respect to the stretchable direction ED (WD) is 2.0 to 20.0 mm, preferably 3.0 to 15.0 mm, particularly preferably 4.0 to 10.0 mm.

Furthermore, as a distance with respect to the orthogonal direction LD determined by a mutual relationship between adjacent first joined portions 40 and 40 in the row of the first joined portions 40, 40 . . . , it is desirable that a percentage R of a ratio of (a separation distance d between adjacent first joined portions)/(a distance P from one point of a joined portion to one corresponding point of an adjacent first joined portion) is set to 5 to 60%, preferably 10 to 45%, and particularly 20 to 35%.

When this percentage is excessively high, in the case of application to a product, the stretching stress in the width direction (stretchable direction) is high, and it tends to be difficult to obtain suitable fitting as a wearing article.

In addition, when the percentage is excessively low, a possibility that the first joined portions 40 and 40 adjacent to each other in the orthogonal direction LD are continuous in a manufacturing process may not be excluded, and more fundamentally, an anvil and a heating horn that form the joined portions are excessively burdened with equipment, which may be a cause of hindering stable operation.

It is desirable that a joined portion having the length L of the first joined portion 40 or a longer length is not formed in the row of the second joined portions 41 and 41.

The second example exhibits typically the following advantages and features.

(1) Since the percentage R is low, an elastic sheet member having a low stretching stress in the stretchable direction and having a flexible elongation is obtained, and when this elastic sheet member is applied to an absorbent article, a feeling of wearing is excellent.

In addition, since an opening ratio is increased, the air permeability is increased.

(2) Since not only the row of the first joined portions 40, 40 . . . but also the row of the second joined portions 41, 41 . . . is formed, inter-row pleats R can be formed between the row of the first joined portions 40, 40 . . . and the row of the second joined portions 41, 41 . . . . In the above embodiment illustrated in FIG. 11, when viewed from a viewpoint of design as the entire stretchable region of the product, the wrinkle 25F long in the orthogonal direction LD is merely formed with uniform repetition in the stretchable direction ED (WD), the design is prone to become simple, and product appeal tends to be poor. However, the design can be improved by forming the inter-row pleats R as in the second example.

(3) The second joined portions 41 have a smaller area than that of the first joined portions 40, and thus look like a pattern.

(4) A statement that the inter-row pleats R can be formed between the row of the first joined portions 40, 40 . . . and the row of the second joined portions 41, 41 . . . means that two inter-row pleats can be formed between the row of the first joined portions 40, 40 . . . and the row of the first joined portions 40, 40 . . . . However, since a distance between the second joined portions 41 and 41 is long in the row of the second joined portions 41, 41 . . . , the statement means that pleats can be formed without excessively burdening the anvil and the heating horn with equipment. As a result, when compared to a case in which the inter-row pleats are formed only by the row of the first joined portions 40, 40 . . . as illustrated in FIG. 11, a large number of pleats can be formed with a narrow width per unit area without burdening the equipment.

Thus, a contact area of the wearer with the skin can be reduced, and comfort and softness can be improved.

Third Example

As illustrated in FIG. 13, a group of the second joined portions 41, 41 . . . can be disposed between the first joined portions 40 and 40 in the orthogonal direction LD. In this case, even when the length L of the first joined portion 40 is short, the second joined portions 41 are positioned, so that the stretching stress can be reduced.

Fourth Example

As illustrated in FIG. 14, for example, it is possible to adopt a mode in which one second joined portion 41 is disposed adjacent to two first joined portions 40 and 40 rather than arranging the second joined portion 41 adjacent to the first joined portion 40 on a one-to-one basis.

Fifth Example

As illustrated in FIG. 15, it is possible to form a row of third joined portions 42, 42 . . . having a long separation interval in the orthogonal direction LD between the row of the first joined portions 40, 40 . . . and the row of the second joined portions 41, 41 . . . .

By forming the third joined portion 42, it is possible to form large pleats bf obtained by dividing the inter-row pleats R shown in the first example in the orthogonal direction LD.

A small pleat sf can be formed between the third joined portion 42 and the row of the first joined portions 40, 40 . . . .

A pleat group obtained by dividing the inter-row pleats R has a low bending rigidity (easy to bend) of the elastic member and an excellent following ability with respect to movement of the body.

Sixth Example

As illustrated in FIG. 16, by obliquely arranging the positions of the third joined portions 42 together with the second joined portions 41, a group of large pleats bf in an oblique array can be formed, and designability is high.

Seventh Example

As illustrated in FIG. 17, fourth joined portions 43 can be inserted and disposed in the row of the first joined portions 40, 40 . . . . In this case, the fourth joined portions 43, 43 . . . can be disposed along the stretchable direction ED or obliquely as illustrated in the figure. In this case, the area of the fourth joined portion 43 is preferably 5% or more and 50% or less of the area of the first joined portion 40.

Eighth Example

As illustrated in FIG. 18, the first joined portions 40 may be inclined. The second joined portions 42 may be inclined.

In the invention, since the length of the joined portion is based on the orthogonal direction LD, as illustrated in FIG. 18, the length L of the first joined portion 40 corresponds to a length in the orthogonal direction LD from a center of one side to a central portion of the other side.

With regard to the separation interval, a distance in the orthogonal direction LD between a center of a side and a center of a side facing the side corresponds to the separation distance d.

Ninth Example

FIG. 19 illustrates an example in which both the first joined portions 40 and the second joined portions 42 are inclined, and each row of the joined portions is inclined at an intersection angle θ with respect to the stretchable direction ED in a range of 30 degrees to 150 degrees, desirably 45 degrees to 135 degrees without extending along the orthogonal direction LD. The intersection angle θ is particularly preferably 60 degrees to 120 degrees. However, these angle ranges indicating inclination do not include 90 degrees as a matter of course.

An advantage of this joined portion row inclined to intersect the stretchable direction ED without extending in the orthogonal direction LD is clear when the eighth example illustrated in FIG. 18 is compared. That is, in the example illustrated in FIG. 19, the fact that, for example, the separation interval between the first joined portions 40 and 40 on a line in the orthogonal direction LD is considerably larger than that of the eighth example illustrated in FIG. 18 brings a benefit.

That is, for example, it is desirable that the first sheet layer 20A and the second sheet layer 20B are bonded to each other in the sheet joined portions 40 using bonding means by material welding such as heat sealing or ultrasonic sealing.

In the case of continuous production, seal melting is performed between an anvil roll and an ultrasonic horn using ultrasonic waves. To prevent energy loss, it is important that the ultrasonic horn is in close contact with the sheet in the entire anvil roll in axial direction. In the case of forming a pattern having a large proportion of anvil roll convex such as the row of the joined portions 40, 40 . . . of FIG. 12 along a bus line in line contact for this purpose, it is necessary to output large ultrasonic waves. When an excessive tightening force is applied along the bus line in line contact for this purpose, a burden on an equipment side is large.

On the other hand, in the case of the ninth example illustrated in FIG. 19 (generally in the case of an inclined arrangement), a proportion occupied by the joined portions located on a line in the orthogonal direction LD is small, resulting in a stable linear pressure. Thus, the equipment burden is small, and stable operation can be performed.

In the ninth example illustrated in FIG. 19, since the first joined portions 40 (and the second joined portions 42) are inclined, there is an advantage that it is possible to form pleats excellent in designability.

The shapes of the individual sheet joined portions 40 and joint holes 31 in the natural length state can be determined as appropriate in addition to the above-described rectangle. For example, in addition to a convex lens shape (see FIG. 20(a)), a rhombus shape (see FIG. 20(b)), a concave lens shape (see FIG. 20(c)), and an elliptical shape (see FIG. 20(d)) as exemplified in FIG. 20, it is possible to adopt any shape such as a perfect circle, a triangle, a polygon, a star shape, a cloud shape, etc.

The joint holes 31 mainly relate to the shape of the joined portions 40 (41, 42, and 43) and a manufacturing stage or a degree of stretching/contraction.

When the first sheet layer 20A and the second sheet layer 20B are bonded in the sheet joined portions 40 through the joint holes 31 formed in the elastic film 30, it is desirable that the first sheet layer 20A and the second sheet layer 20B are not bonded to the elastic film 30 except at least between the first sheet layer 20A and the second sheet layer 20B in the sheet joined portions 40.

Bonding means for the first sheet layer 20A and the second sheet layer 20B in the sheet joined portions 40 is not particularly limited. For example, the first sheet layer 20A and the second sheet layer 20B may be bonded to each other in the sheet joined portions 40 using a hotmelt adhesive or using bonding means by material welding such as heat sealing or ultrasonic sealing.

In a case in which the first sheet layer 20A and the second sheet layer 20B are bonded through the joint holes 31 of the elastic film 30 in the sheet joined portions 40, as a mode in which the sheet joined portions 40 are formed by material welding, it is possible to adopt any one of a first welding mode in which the first sheet layer 20A and the second sheet layer 20B are bonded only by a molten and solidified material 20m of a most part or a part of at least one of the first sheet layer 20A and the second sheet layer 20B in the sheet joined portions 40 (see FIG. 21(a)), a second welding mode in which the first sheet layer 20A and the second sheet layer 20B are bonded only by a molten and solidified material 30m of all, a most part, or a part of the elastic film 30 in the sheet joined portions 40 (see FIG. 21(b)), and a third welding mode in which both of these modes are combined (see FIG. 21(c)), and the second and third welding modes are preferable.

A particularly preferable mode is that the first sheet layer 20A and the second sheet layer 20B are bonded by the molten and solidified material 20m of the part of the first sheet layer 20A and the second sheet layer 20B and the molten and solidified material 30m of all or the most part of the elastic film 30 in the sheet joined portions 40. Incidentally, in the third welding mode illustrated in FIG. 23(b), the molten and solidified material 30m of the elastic film 30 shown in white is seen between fiber molten and solidified materials 20m of the first sheet layer 20A or the second sheet layer 20B shown in black. On the other hand, in the first welding mode illustrated in FIG. 23(a), the molten and solidified material of the elastic film is not seen between fiber molten and solidified materials 20m of the first sheet layer 20A or the second sheet layer 20B.

When the first sheet layer 20A and the second sheet layer 20B are bonded using the molten and solidified material 20m of the most part or the part of at least one of the first sheet layer 20A and the second sheet layer 20B as an adhesive as in the first adhesive mode or the third adhesive mode, it is preferable that a part of the first sheet layer 20A and the second sheet layer 20B is not melted since the sheet joined portions 40 are not hardened.

Incidentally, when the first sheet layer 20A and the second sheet layer 20B are nonwoven fabrics, a case in which a part of the first sheet layer 20A and the second sheet layer 20B does not melt includes a mode in which cores (including a central part of a single component fiber in addition to a core in a composite fiber) are left for all fibers of the sheet joined portions 40 while a surrounding part thereof (including a part of a surface layer side of the single component fiber in addition to a sheath in the composite fiber) melts, and a mode in which even though some fibers do not melt at all, remaining fibers all melt or even though cores are left, a surrounding part thereof melts.

When the first sheet layer 20A and the second sheet layer 20B are bonded using the molten and solidified material 30m of the elastic film 30 as an adhesive as in the second welding mode and the third welding mode, peel strength becomes high. In the second welding mode, under the condition that a melting point of at least one of the first sheet layer 20A and the second sheet layer 20B is higher than a melting point of the elastic film 30 and a heating temperature at the time of forming the sheet joined portions 40, the elastic film 30 is interposed between the first sheet layer 20A and the second sheet layer 20B, a site corresponding to the sheet joined portions 40 is pressurized and heated, and only the elastic film 30 is melted. In this way, manufacturing can be performed.

Meanwhile, in the third welding mode, under the condition that a melting point of at least one of the first sheet layer 20A and the second sheet layer 20B is higher than a melting point of the elastic film 30, the elastic film 30 is interposed between the first sheet layer 20A and the second sheet layer 20B, a site corresponding to the sheet joined portions 40 is pressurized and heated, and at least one of the first sheet layer 20A and the second sheet layer 20B and the elastic film 30 are melted. In this way, manufacturing can be performed.

From such a viewpoint, the melting point of the elastic film 30 is preferably about 80 to 145° C., the melting point of the first sheet layer 20A and the second sheet layer 20B is preferably about 85 to 190° C., particularly 150 to 190° C., and a difference between the melting point of the first sheet layer 20A and the second sheet layer 20B and the melting point of the elastic film 30 is preferably about 60 to 90° C. In addition, the heating temperature is preferably set to about 100 to 150° C.

In the second welding mode and the third welding mode, when the first sheet layer 20A and the second sheet layer 20B are nonwoven fabrics, the molten and solidified material 30m of the elastic film 30 may penetrate between fibers over the entire first sheet layer 20A and second sheet layer 20B in the thickness direction in the sheet joined portions 40 as illustrated in FIG. 22(c). However, in a mode in which the molten and solidified material 30m penetrates between the fibers to the middle in the thickness direction as illustrated in FIG. 22(a), or a mode in which the molten and solidified material 30m hardly penetrates between the fibers of the first sheet layer 20A and the second sheet layer 20B as illustrated in FIG. 22(b), flexibility of the sheet joined portions 40 becomes high.

FIG. 24 illustrates an example of an ultrasonic sealing device suitable for forming the second welding mode and the third welding mode. In this ultrasonic sealing device, when the sheet joined portions 40 are formed, the first sheet layer 20A, the elastic film 30, and the second sheet layer 20B are fed between an anvil roll 60 having projections 60a formed in the pattern of the sheet joined portions 40 on an outer surface and an ultrasonic horn 61. At this time, for example, by setting a feeding speed of the upstream elastic film 30 by a feed drive roll 63 and a nip roll 62 to be lower than a feeding speed on the downstream side of the anvil roll 60 and the ultrasonic horn 61, the elastic film 30 is stretched to a predetermined stretch rate in an MD (machine direction, flow direction) through a path from a nip position by the feed drive roll 63 and the nip roll 62 to a seal position by the anvil roll 60 and the ultrasonic horn 61. The stretch rate of the elastic film 30 can be set by selecting a speed difference between the anvil roll 60 and the feed drive roll 63, and can be set to about 300% to 500%, for example. Reference character 62 indicates the nip roll.

The first sheet layer 20A, the elastic film 30, and the second sheet layer 20B fed between the anvil roll 60 and the ultrasonic horn 61 are heated by ultrasonic vibration energy of the ultrasonic horn 61 while being pressurized between the projections 60a and the ultrasonic horn 61 in a state of being stacked in this order. By melting only the elastic film 30 or melting at least one of the first sheet layer 20A and the second sheet layer 20B and the elastic film 30, the joint holes 31 are formed in the elastic film 30. At the same time, the first sheet layer 20A and the second sheet layer 20B are bonded through the joint holes 31. Therefore, in this case, by selecting a size, a shape, a separation interval, and an arrangement pattern in a roll length direction and a roll circumferential direction of the projections 60a of the anvil roll 60, it is possible to select an area ratio of the sheet joined portions 40.

A reason why the joint holes 31 are formed may not be clear. However, it is considered that the holes are formed when portions corresponding to the projections 60a of the anvil roll 60 in the elastic film 30 are melted and detached from the surroundings. In this instance, a portion between adjacent joint holes 31 aligned in the stretchable direction ED in the elastic film 30 is cut from portions on both sides in the stretchable direction by the joint holes 31 as illustrated in FIG. 9(a) and FIG. 11(a), and loses support on both sides in a contracting direction. Thus, in a range in which continuity in a direction orthogonal to the contracting direction can be maintained, a center side in the direction LD orthogonal to the stretchable direction ED more contracts until the center side is balanced with a center side in the stretchable direction, and the joint holes 31 enlarge in the stretchable direction ED.

A constituent material of the first sheet layer 20A and the second sheet layer 20B can be used without particular limitation as long as the constituent material is a sheet-like material. However, it is preferable to use a nonwoven fabric from a viewpoint of air permeability and flexibility. A row material of the nonwoven fabric is not particularly limited. For example, examples thereof may include a polyolefin-based synthetic fiber such as polyethylene or polypropylene, a polyester-based synthetic fiber, a polyamide-based synthetic fiber, etc., a recycled fiber such as rayon or cupra, a natural fiber such as cotton, or a mixed fiber, a composite fiber, etc. in which two or more of these materials are used. Further, the nonwoven fabric may be manufactured by any processing.

Examples of a processing method may include a known method, for example, a spunlace method, a spunbond method, a thermal bond method, a meltblown method, a needle punch method, an air through method, a point bond method, etc. In the case of using a nonwoven fabric, a basis weight is preferably set to about 10 to 25 g/m$^2$. Further, a part or all of the first sheet layer 20A and the second sheet layer 20B may correspond to a pair of layers faced to each other by folding a single material. For example, as in the illustrated embodiment, in the waist end portions 23, a constituent material located on the outside may be used as the second sheet layer 20B, a folded portion 20C folded back to an internal surface side at a waist opening edge thereof may be used as the first sheet layer 20A, and the elastic film 30 may be interposed therebetween. Further, in other portions, a constituent material located on the inside may be used as the first sheet layer 20A, a constituent material located on the outside may be used as the second sheet layer 20B, and the elastic film 30 may be interposed therebetween. Naturally, the constituent material of the first sheet layer 20A and the constituent material of the second sheet layer 20B may be individually provided over the entire region in the front-back direction LD, and the elastic film 30 may be interposed between the constituent material of the first sheet layer 20A and the constituent material of the second sheet layer 20B without folding back the constituent materials.

The elastic film 30 is not particularly limited. As long as the elastic film 30 is a thermoplastic resin film having elasticity, in addition to a non-perforated film, it is possible to use a film in which a plurality of holes or slits is formed for ventilation. In particular, it is preferable that the elastic film 30 has a tensile strength in the width direction WD (stretchable direction ED, MD) of 8 to 25 N/35 mm, a tensile strength in the front-back direction LD (direction LD orthogonal to the stretchable direction, CD (cross direction)) of 5 to 20 N/35 mm, a tensile elongation in the width direction WD of 450 to 1,050%, and a tensile elongation in the front-back direction LD of 450 to 1,400%. A thickness of the elastic film 30 is not particularly limited. However, the thickness is preferably about 20 to 40 μm.

(Stretchable Region)

A region having the elastic sheet stretchable structure 20X in the outer member 20 has a stretchable region that can be stretched and contracted in the width direction WD. In a stretchable region 80, the elastic film 30 has a portion 32 (see FIG. 12(a)) that is linearly continuous along the width direction WD, which is contracted in the width direction WD by the contraction force of the elastic film 30 and in extensible in the width direction WD. More specifically, in a state where the elastic film 30 is stretched in the width direction WD, the first sheet layer 20A and the second sheet layer 20B are bonded through the joint holes 31 of the elastic film 30 at intervals in each of the width direction WD and the front-back direction LD orthogonal thereto (the direction LD orthogonal to the stretchable direction) to form a plurality of sheet joined portions 40, thereby forming the elastic sheet stretchable structure 20X. Further, in the stretchable region 80, the joint holes 31 are disposed so that the elastic film 30 has the portion 32 (see FIG. 12(a)) that is linearly continuous along the width direction WD, thereby imparting such elasticity.

In the stretchable region, the first sheet layer 20A and the second sheet layer 20B between the sheet joined portions 40 swell in a direction in which they are separated from each other, thereby forming contraction wrinkles 25f and 25F extending in the front-back direction LD in the natural length state as illustrated in FIG. 9 and FIG. 12(b). Further, in a worn state of being stretched to some extent in the width direction WD, the contraction wrinkles 25F are left even though the contraction wrinkles 25F are extended. In addition, as in the illustrated embodiment, when the first sheet layer 20A and the second sheet layer 20B are not bonded to the elastic film 30 at least in a portion other than between the first sheet layer 20A and the second sheet layer 20B in the sheet joined portions 40, gaps are formed between the joint holes 31 and the sheet joined portions 40 in the elastic film 30, as can be seen from FIG. 9(c) assuming a worn state and FIG. 9(a) assuming an unfolded state of the first sheet layer 20A and the second sheet layer 20B, in these states. Even when the material of the elastic film 30 is a non-porous film or sheet, air permeability is imparted by the gaps. Further, in the natural length state, the joint holes 31 are squeezed due to further contraction of the elastic film 30, and a gap is hardly formed between the joint holes 31 and the sheet joined portions 40.

It is desirable that an elongation at elastic limit of the stretchable region 80 in the width direction WD is 190% or more (preferably 225 to 285%). The elongation at elastic limit of the stretchable region 80 is substantially determined by the stretch rate of the elastic film 30 at the time of manufacture, and the elastic limit elongation decreases due to factors that inhibit contraction in the width direction WD based thereon. A main factor of such inhibition is a ratio of the length L of the sheet joined portions 40 per unit length in the width direction WD, and the elongation at elastic limit decreases as this ratio increases. In a normal case, since the length L of the sheet joined portions 40 has a correlation with an area ratio of the sheet joined portions 40, the elongation at elastic limit of the stretchable region 80 can be adjusted by the area ratio of the sheet joined portions 40.

The stretching stress of the stretchable region 80 can be mainly adjusted by a sum of an orthogonal direction LD distance (separation distance d) of the portion 32 (FIG. 12(a)) in which the elastic film 30 linearly continues along the width direction WD.

The area ratio of the sheet joined portions 40 and the area of each of the sheet joined portions 40 in the stretchable region 80 can be determined as appropriate and are preferably within the following ranges in a normal case.

Area of each of sheet joined portions 40: 0.14 to 3.5 mm$^2$ (particularly 0.14 to 1.0 mm$^2$)

Area ratio of sheet joined portions 40: 1.8 to 19.1% (particularly 1.8 to 10.6%)

As described above, the elongation at elastic limit and stretching stress of the stretchable region 80 can be adjusted by the area of the sheet joined portions 40. Thus, as illustrated in FIG. 7, a plurality of regions having different area ratios of the sheet joined portions 40 may be provided in the stretchable region 80 to change fitting according to the site. In the embodiment illustrated in FIG. 7, edge portion stretchable regions 82 of leg openings are provided, and the edge portion stretchable regions 82 are set as flexibly stretching regions in which an area ratio of the sheet joined portions 40 is higher than that of other regions, and thus stretching stress is weak.

(Non-Stretchable Region)

In a region having the elastic sheet stretchable structure 20X in the outer member 20, as illustrated in FIG. 7, a non-stretchable region 70 may be provided at least on one side of the stretchable region 80 in the width direction. Arrangement of the stretchable region 80 and the non-stretchable region 70 can be determined as appropriate. In the case of the outer member 20 of the underpants-type disposable diaper as in the present embodiment, a portion overlapping the absorbent body 13 is a region not requiring stretching and contraction. Thus, as in the illustrated embodiment, it is preferable to form a part or all of the portion overlapping the absorbent body 13 (it is desirable to include almost the entire inner/outer fixing region 10B) into the non-stretchable region 70. Naturally, the non-stretchable region 70 may be provided from a region overlapping the absorbent body 13 to a region not overlapping the absorbent body 13 away from the region in the width direction WD or the front-back direction LD, and the non-stretchable region 70 may be provided only in the region not overlapping the absorbent body 13.

The non-stretchable region 70 is a region not having the portion that linearly continues along the width direction WD due to the presence of the joint holes 31 even though the elastic film 30 is continuous in the width direction WD. Therefore, even though in a state where the elastic film 30 is stretched in the width direction WD, the first sheet layer 20A and the second sheet layer 20B are bonded through the joint holes 31 of the elastic film 30 at intervals in each of the width direction WD and the front-back direction LD orthogonal thereto, and a plurality of sheet joined portions 40 is formed, thereby forming the entire elastic sheet stretchable structure 20X including both the stretchable region 80 and the non-stretchable region 70, the elastic film 30 is not linearly continuous along the width direction WD in the non-stretchable region 70. Thus, the contraction force of the elastic film 30 hardly acts on the first sheet layer 20A and the second sheet layer 20B, the elasticity is almost lost, and the elongation at elastic limit is close to 100%.

In such a non-stretchable region 70, the first sheet layer 20A and the second sheet layer 20B are bonded by a plurality of sheet joined portions 40 arranged at intervals, and the sheet joined portions 40 are not continuous. Thus, a decrease in flexibility is prevented.

An arrangement pattern of the joint holes 31 in the elastic film 30 in the non-stretchable region 70 can be determined as appropriate.

The area ratio of the sheet joined portions 40 and the area of each of the sheet joined portions 40 in the non-stretchable region can be determined as appropriate. However, in a normal case, the area ratio and the area are preferably within the following ranges since the non-stretchable region 70 does not become hard due to the small area of each of the sheet joined portions 40 and the low area ratio of the sheet joined portions 40.

Area of each of sheet joined portions 40: 0.10 to 0.75 mm$^2$ (particularly 0.10 to 0.35 mm$^2$)

Area ratio of sheet joined portions 40: 4 to 13% (particularly 5 to 10%)

In the above example, the elastic film is used as the elastic sheet. However, an elastic nonwoven fabric may be used. Further, an elastic nonwoven fabric may be provided on one side or both sides of the elastic film, which may be interposed between the first sheet layer 20A and the second sheet layer 20B.

Description of Terms in Specification

The following terms in the specification have the following meanings unless otherwise specified in the specification.

The "front body" and the "back body" refer to portions on the front side and the back side, respectively, with respect to a center of the underpants-type disposable diaper in the front-back direction as a boundary. In addition, the crotch portion refers to a range in the front-back direction including the center of the underpants-type disposable diaper in the front-back direction, and refers to a range of a portion having a narrowing portion in the front-back direction when the absorbent body has the narrowing portion.

The "elongation at elastic limit" refers to an elongation of an elastic limit (in other words, a state in which the first sheet layer and the second sheet layer are fully unfolded) in the stretchable direction ED, and represents a length at the time of the elastic limit as a percentage when the natural length is 100%.

The "area ratio" refers to a ratio of a target portion to a unit area, and is represented as a percentage of a value obtained by dividing a total area of target portions (for example, the sheet joined portions 40, the openings of the joint holes 31, and the vent holes) in target regions (for example, the stretchable region 80 and the non-stretchable region 70) by an area of the target regions. In particular, the "area ratio" in a region having the stretchable structure refers to an area ratio in a state of being stretched to the elastic limit in the stretchable direction ED. In a mode in which a plurality of target portions is provided at intervals, it is desirable to obtain the area ratio by setting a size of the target regions to include ten or more target portions.

The "stretch rate" refers to a value when the natural length is 100%.

The "basis weight" is measured as below. A sample or a test piece is pre-dried, and then is left in a test room or a device in a standard state (temperature 23±1° C., relative humidity 50±2% in a test location), and is put in a constant weight state. Pre-drying refers to setting the weight of the sample or the test piece to a constant weight in an environment in which temperature is 100° C. Incidentally, pre-drying is unnecessary for a fiber having an official moisture regain of 0.0%. A sample having dimensions of 100 mm×100 mm is cut off from the test piece in the constant weight state using a sampling template (100 mm×100 mm). A weight of the sample is measured and multiplied by 100 to calculate a weight per square meter, and the weight is set to the basis weight.

The "thickness" of the absorbent body is measured using a thickness measuring instrument of Ozaki Mfg. Co., Ltd. (Peacock, Dial Thickness Gauge Large Type, Model J-B (measurement range 0 to 35 mm) or Model K-4 (measurement range 0 to 50 mm)) by horizontally placing the sample and the thickness measuring device. A "thickness" other than the above thickness is automatically measured under the condition of load: 0.098 $N/cm^2$ and pressure area: 2 $cm^2$ using an automatic thickness meter (KES-G5 handy compression measurement program).

The "tensile strength" and the "tensile elongation (breaking elongation) refer to values measured by setting an initial chuck interval (distance between marked lines) to 50 mm and a tensile speed to 300 mm/min in accordance with JIS K7127: 1999 "Plastics-Determination of tensile properties-" except that the test piece has a rectangular shape of width 35 mm×length 80 mm. As a tensile testing machine, for example, AUTOGRAPH AGS-G100N manufactured by SHIMADZU CORPORATION can be used.

The "stretching stress" refers to the tensile stress (N/35 mm) measured when stretching in the elastic region by a tensile test setting an initial chuck interval (distance between marked lines) to 50 mm and a tensile speed to 300 mm/min in accordance with JIS K7127: 1999 "Plastics-Determination of tensile properties-", and a degree of stretching can be appropriately determined depending on the test object. It is preferable that the test piece has a rectangular shape having a width of 35 mm and a length of 80 mm or more. However, when a test piece having a width of 35 mm may not be cut out, the test piece is created to have a width allowing cutting out, and a measured value is set to a value converted to have the width of 35 mm. In addition, even in a case in which the target region is small and sufficient test pieces may not be collected, when the magnitude of stretching stress is compared, even a suitably small test piece can be compared at least as long as test pieces of the same size are used. As a tensile testing machine, for example, AUTOGRAPH AGS-G100N manufactured by SHIMADZU CORPORATION can be used.

The "unfolded state" refers to a flatly unfolded state without contraction or slack.

Dimensions of each portion refer to dimensions in an unfolded state rather than the natural length state unless otherwise stated. In particular, the dimension of the joined portion is a dimension in a state where the joined portions are unfolded to the limit (state before the first sheet layer and the second sheet layer are broken), and substantially coincides with a joined portion pattern dimension in the anvil roll.

When there is no description about an environmental condition in a test or measurement, it is presumed that the test or measurement is performed in a test room or a device in a standard state (temperature 23±1° C., relative humidity 50±2% in a test location).

INDUSTRIAL APPLICABILITY

As long as a stretchable region to which an elastic sheet stretchable structure can be applied is included, the invention can be used for disposable wearing articles in general such as various disposable diapers of a tape type, a pad type, etc., a sanitary napkin, a disposable wearing article for swimming or playing in the water, etc. in addition to the underpants-type disposable diaper as in the above example.

REFERENCE SIGNS LIST

10 Inner member
10B Inner/outer fixing region
11 Top sheet
12 Liquid impervious sheet
13 Absorbent body 13N Narrower portion
14 Package sheet
17 Non-absorbent body side portion
20 Outer member
20A First sheet layer
20B Second sheet layer
20C Folded portion
20X Elastic sheet stretchable structure
21 Side seal portion
23 Waist end portion
24 Waist portion elastic member
25F, 25f Contraction wrinkles
29 Around-leg line
30 Elastic film
31 Joint hole
33 Vent hole
40, 40A, 40B Sheet joined portion (first joined portion)
41 Second joined portion
42 Third joined portion
43 Fourth joined portion
70 Non-stretchable region
80 Stretchable region
82 Edge portion stretchable region
90 Three-dimensional gather
93 Fallen portion
94 Free portion
95 Gather sheet
96 Gather elastic member
B Back body
ED Stretchable direction (width direction)
F Front body
L Intermediate portion
LD Orthogonal direction (front-back direction)
T Lower torso portion
sf Small pleat
bf Large pleat
Px Separation distance
Py Separation distance
E1 First stretchable region
E2 Second stretchable region
E3 Intermediate region

The invention claimed is:

1. An elastic member having an elastic sheet stretchable structure in which an elastic sheet is interposed between a first sheet layer and a second sheet layer and the first sheet layer and the second sheet layer are bonded directly via joint holes penetrating the elastic sheet or indirectly via the elastic sheet forming a plurality of joined portions,
   wherein a region having the elastic sheet stretchable structure includes a stretchable region that contracts in a stretchable direction by contraction of the elastic sheet and is extensible in the stretchable direction,
   wherein the joined portions are formed in the stretchable region and arranged in a pattern in the stretchable direction and an orthogonal direction thereto, and
   wherein, in an unfolded state of the elastic sheet stretchable structure without contraction or slack, the pattern of the plurality of joined portions comprises:
      first joined portions and second joined portions, each of the second joined portions having an area smaller than an area of each of the first joined portions,
      the first joined portions are formed in staggered rows of first joined portions having a separation pitch between adjacent rows in the stretchable direction, wherein each of the first joined portions comprise an elongated shape substantially aligned along a row direction, such that a direction of elongation is either orthogonal to the stretchable direction or inclined at an inclination angle of 60 to 120 degrees with respect to thereto,
      the second joined portions are formed in rows alternating with the rows of first joined portions, and
      wherein the arrangement of the rows of first joined portions and rows of second joined portions is such that a plurality of stretchable direction lines containing no joined portions are formed in the orthogonal direction, each having a width in the orthogonal direction measured between an elongate end of a first joined portion and either an elongate end of a first joined portion in an adjacent row of first joined portions or an end of a second joined portion in an adjacent row of second joined portions being greater than 0 and 0.5 mm or less, and a plurality of oblique lines containing no joined portions are formed in the orthogonal direction each having a predetermined width in the orthogonal direction and intersecting the stretchable direction at an angle of 45 degrees or less.

2. The elastic member according to claim 1, wherein the pattern of joined portions further comprises third joined portions in a plurality of rows along at least one of the orthogonal direction, the stretchable direction, or an oblique direction thereto, each of the third joined portions having a smaller area than the area of each of the first joined portions and identical to or different than the area of each of the second joined portions.

3. The elastic member according to claim 2, wherein the pattern of joined portions further comprises fourth joined portions inserted and disposed in the rows of first joined portions, wherein the area of each of the fourth joined portions is 5% or more and 50% or less of the area of each of the first joined portions.

4. The elastic member according to claim 1, wherein a percentage ratio of the width of the stretchable direction lines to a distance P from a point of one of the first joined portions to a corresponding point of another of the first joined portions in an adjacent row is 5% to 60%.

5. The elastic member according to claim 1, wherein the separation pitch is 2.0 to 20.0 mm.

6. The elastic member according to claim 1, wherein a total area ratio of the pattern of the plurality of joined portions is 1.8% to 19.5% with respect to the stretchable region.

7. The elastic member according to claim 1, wherein an area of each of the joined portions is 0.14 to 3.5 mm$^2$.

8. The elastic member according to claim 1, wherein the first sheet layer and the second sheet layer are nonwoven fabrics.

9. An underpants-type disposable wearing article comprising:
   an integrated outer member covering from a front body to a back body or outer members separately provided for the front body and the back body;
   an inner member attached to an intermediate portion of the outer member in a width direction to extend to both front and back sides of a crotch portion;
   side seal portions in which both side portions of the outer member in the front body and both side portions of the outer member in the back body are bonded to each other;
   and a waist opening and a pair of right and left leg openings, wherein the outer member in at least one of the front body and the back body is the elastic member according to claim 1.

10. An elastic member having an elastic sheet stretchable structure in which an elastic sheet is interposed between a first sheet layer and a second sheet layer and the first sheet layer and the second sheet layer are bonded directly via joint holes penetrating the elastic sheet or indirectly via the elastic sheet forming a plurality of joined portions,
   wherein a region having the elastic sheet stretchable structure includes a stretchable region that contracts in a stretchable direction by contraction of the elastic sheet and is extensible in the stretchable direction, wherein the joined portions are formed in the stretchable region and arranged in a pattern in the stretchable direction and a n orthogonal direction thereto, and
   wherein, in an unfolded state of the elastic sheet stretchable structure without contraction or slack, the pattern of the plurality of joined portions comprises:
      first joined portions and second joined portions, each of the second joined portions having an area smaller than an area of each of the first joined portions,
      the first joined portions are formed in staggered rows of first joined portions having a separation pitch between adjacent rows in the stretchable direction, wherein each of the first joined portions comprise an elongated shape substantially aligned along a row direction, such that a direction of elongation is either orthogonal to the stretchable direction or inclined at an inclination angle of 60 to 120 degrees with respect to thereto,
      the second joined portions are formed in a plurality of rows alternating with the rows of first joined portions, and
      wherein the arrangement of the rows of first joined portions and rows of second joined portions is such that a plurality of stretchable direction lines are located in the orthogonal direction each intersecting one of the first joined portions and another of the first joined portions in an adjacent row multiple times along the stretchable direction, and a plurality of oblique lines containing no joined portions are formed each having a predetermined width in the orthogonal direction being 0.6 to 10.0 mm and intersecting the stretchable direction at an angle of 45 degrees or less.

11. The elastic member according to claim 10, wherein the separation pitch is 2.0 to 20.0 mm.

12. The elastic member according to claim 10, wherein a total area ratio of the pattern of the plurality of joined portions is 1.8% to 19.5% with respect to the stretchable region.

13. The elastic member according to claim 10, wherein an area of each of the joined portions is 0.14 to 3.5 mm$^2$.

14. The elastic member according to claim 10, wherein the first sheet layer and the second sheet layer are nonwoven fabrics.

15. An underpants-type disposable wearing article comprising:
   an integrated outer member covering from a front body to a back body or outer members separately provided for the front body and the back body;
   an inner member attached to an intermediate portion of the outer member in a width direction to extend to both front and back sides of a crotch portion;
   side seal portions in which both side portions of the outer member in the front body and both side portions of the outer member in the back body are bonded to each other;
   and a waist opening and a pair of right and left leg openings, wherein the outer member in at least one of the front body and the back body is the elastic member according to claim 10.

\* \* \* \* \*